(12) United States Patent
El Sayed et al.

(10) Patent No.: US 12,002,203 B2
(45) Date of Patent: Jun. 4, 2024

(54) SYSTEMS AND METHODS FOR ASSESSING A LIKELIHOOD OF CTEPH AND IDENTIFYING CHARACTERISTICS INDICATIVE THEREOF

(71) Applicant: BAYER HEALTHCARE LLC, Whippany, NJ (US)

(72) Inventors: Karym El Sayed, Berlin (DE); Henry Hernaez, Pittsburgh, PA (US); Nivitha Mahesh, Murrysville, PA (US); Wei Liao, Frankfurt am Main (DE); Franco Fois, Monheim (DE); Daniel Rechsteiner, Cologne (DE); Jacob Agris, Great Neck Estates, NY (US); Mohammad Sedigh Ghamari, Jersey City, NJ (US); Xiangzhen Gao, Sterling Heights, MI (US); Prahlad Menon Gopalakrishna, Bethel Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 348 days.

(21) Appl. No.: 17/434,839

(22) PCT Filed: Mar. 10, 2020

(86) PCT No.: PCT/US2020/021861
§ 371 (c)(1),
(2) Date: Aug. 30, 2021

(87) PCT Pub. No.: WO2020/185758
PCT Pub. Date: Sep. 17, 2020

(65) Prior Publication Data
US 2022/0148166 A1    May 12, 2022

Related U.S. Application Data

(60) Provisional application No. 62/817,295, filed on Mar. 12, 2019.

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/12* (2017.01); *G06V 10/25* (2022.01);
(Continued)

(58) Field of Classification Search
CPC ......... G16H 30/20; G06T 7/0012; G06T 7/11; G06T 7/12; G06T 7/00;
(Continued)

(56) References Cited

U.S. PATENT DOCUMENTS

| 732,697 A | 7/1903 | Bates |
| 5,732,697 A | 3/1998 | Zhang et al. |

(Continued)

FOREIGN PATENT DOCUMENTS

| CN | 104769641 A | 7/2015 |
| CN | 107492090 A | 12/2017 |

(Continued)

OTHER PUBLICATIONS

Chibuzo; Abonyi et al, "Intravascular Contrast Media in Radiography: Historical Development & Review of Risk Factors for Adverse Reactions", South American Journal of Clinical Research, 2016, Vo. 3, Issue 1.

(Continued)

*Primary Examiner* — Tuan H Nguyen

(74) *Attorney, Agent, or Firm* — James R. Stevenson; Bryan B. Clark

(57) ABSTRACT

Described are systems and methods for assessing a likelihood of chronic thromboembolic pulmonary hypertension (CTEPH) within a subject patient based upon an analysis of (Continued)

characteristics indicative of chronic thromboembolic pulmonary hypertension within an imaging study of the subject patient. The systems and methods can identify characteristics of one or more anatomical structures within a cardiac region of the subject patient indicative of CTEPH, characteristics of a pulmonary vasculature of the subject patient indicative of CTEPH, and characteristics of a chronic abnormality in a lung of the subject patient indicative of CTEPH. The systems and methods can assess these characteristics to compute the likelihood of CTEPH within the subject patient.

21 Claims, 11 Drawing Sheets

(51) Int. Cl.
G06T 7/12 (2017.01)
G06V 10/25 (2022.01)
G06V 10/774 (2022.01)
G16H 30/20 (2018.01)

(52) U.S. Cl.
CPC ............ *G06V 10/774* (2022.01); *G16H 30/20* (2018.01); *G06T 2207/20081* (2013.01); *G06T 2207/30048* (2013.01); *G06T 2207/30061* (2013.01)

(58) Field of Classification Search
CPC . G06T 2207/20081; G06T 2207/30061; G06T 2207/30048; G06V 10/25; G06V 10/774
See application file for complete search history.

(56) References Cited

U.S. PATENT DOCUMENTS

| | | | |
|---|---|---|---|
| 5,840,026 | A | 11/1998 | Uber, III et al. |
| 6,039,931 | A | 3/2000 | Schmitt-Willich et al. |
| 6,643,537 | B1 | 11/2003 | Zatezalo et al. |
| 6,754,376 | B1 | 6/2004 | Turek et al. |
| 6,819,790 | B2 | 11/2004 | Suzuki et al. |
| 7,564,990 | B2 | 7/2009 | Kern et al. |
| 7,738,683 | B2 | 6/2010 | Cahill et al. |
| 7,937,134 | B2 | 5/2011 | Uber et al. |
| 7,949,167 | B2 | 5/2011 | Krishnan et al. |
| 8,060,178 | B2 | 11/2011 | Zhou et al. |
| 8,155,406 | B2 | 4/2012 | Mattiuzzi |
| 9,311,702 | B2 | 4/2016 | Pautot |
| 9,449,381 | B2 | 9/2016 | Liang |
| 9,554,740 | B2 * | 1/2017 | Saeed ............... A61B 5/14551 |
| 9,616,166 | B2 | 4/2017 | Kalafut et al. |
| 9,754,371 | B2 | 9/2017 | Kateb et al. |
| 9,959,615 | B2 | 5/2018 | Liang et al. |
| 10,157,467 | B2 | 12/2018 | Dincer et al. |
| 10,176,408 | B2 | 1/2019 | Paik et al. |
| 10,335,106 | B2 | 7/2019 | Kim |
| 10,555,773 | B2 | 2/2020 | Higaki et al. |
| 10,645,359 | B2 | 5/2020 | Bist et al. |
| 10,933,186 | B2 | 3/2021 | Uber, III |
| 11,246,558 | B2 | 2/2022 | Uber, III et al. |
| 11,308,613 | B2 | 4/2022 | Chitiboi et al. |
| 11,386,553 | B2 * | 7/2022 | Park ........................ G06T 7/11 |
| 2005/0100208 | A1 | 5/2005 | Suzuki et al. |
| 2006/0018524 | A1 | 1/2006 | Suzuki et al. |
| 2007/0047787 | A1 | 3/2007 | Oakley et al. |
| 2008/0317315 | A1 | 12/2008 | Stemmer |
| 2010/0198054 | A1 | 8/2010 | Ewing et al. |
| 2011/0029248 | A1 | 2/2011 | Saeed et al. |
| 2013/0035921 | A1 | 2/2013 | Rodriguez-Ponce et al. |
| 2013/0297554 | A1 | 11/2013 | Mah |
| 2014/0062481 | A1 | 3/2014 | Greiser et al. |
| 2014/0257854 | A1 | 9/2014 | Becker et al. |
| 2015/0125398 | A1 | 5/2015 | Assouline et al. |
| 2016/0000945 | A1 | 1/2016 | Nedergaard et al. |
| 2016/0035093 | A1 | 2/2016 | Kateb et al. |
| 2016/0038092 | A1 | 2/2016 | Golay |
| 2016/0109539 | A1 | 4/2016 | Mardor et al. |
| 2017/0243349 | A1 | 8/2017 | Hou et al. |
| 2017/0245817 | A1 | 8/2017 | Berlin et al. |
| 2017/0269182 | A1 | 9/2017 | Beck |
| 2018/0242917 | A1 | 8/2018 | Bagherzadeh et al. |
| 2018/0315183 | A1 | 11/2018 | Milioni De Carvalho et al. |
| 2019/0012932 | A1 | 1/2019 | Higaki et al. |
| 2019/0099145 | A1 | 4/2019 | Kim |
| 2019/0310338 | A1 | 10/2019 | James et al. |
| 2019/0317171 | A1 | 10/2019 | Nayak et al. |
| 2019/0365340 | A1 | 12/2019 | Hao et al. |
| 2020/0167911 | A1 | 5/2020 | Park et al. |
| 2020/0202557 | A1 | 6/2020 | Schmidt |
| 2020/0258629 | A1 | 8/2020 | Ahmad et al. |
| 2020/0371182 | A1 | 11/2020 | Grimm et al. |
| 2021/0027502 | A1 | 1/2021 | Abumoussa et al. |
| 2022/0018924 | A1 | 1/2022 | Bai et al. |
| 2022/0031270 | A1 | 2/2022 | Cohen et al. |
| 2022/0105265 | A1 | 4/2022 | Cowan et al. |
| 2022/0351369 | A1 | 11/2022 | Haase et al. |

FOREIGN PATENT DOCUMENTS

| | | |
|---|---|---|
| CN | 108324244 A | 7/2018 |
| CN | 109983474 A | 7/2019 |
| EP | 1941460 A1 | 7/2008 |
| EP | 2626718 A1 | 8/2013 |
| EP | 2750102 A1 | 7/2014 |
| EP | 3118644 A1 | 1/2017 |
| EP | 3322997 A1 | 5/2018 |
| EP | 3619631 A1 | 3/2020 |
| EP | 3804615 A1 | 4/2021 |
| EP | 3875979 A1 | 9/2021 |
| JP | 5878009 B2 | 3/2016 |
| KR | 102001398 B1 | 7/2019 |
| WO | 2007053676 A2 | 5/2007 |
| WO | 2009135923 A1 | 11/2009 |
| WO | 2012075577 A1 | 6/2012 |
| WO | 2013121374 A2 | 8/2013 |
| WO | 2014162273 A1 | 10/2014 |
| WO | 2016007734 A1 | 1/2016 |
| WO | 2017040152 A1 | 3/2017 |
| WO | 2017139110 A1 | 8/2017 |
| WO | 2018046412 A1 | 3/2018 |
| WO | 2018183044 A1 | 10/2018 |
| WO | 2018200493 A1 | 11/2018 |
| WO | 2018202541 A1 | 11/2018 |
| WO | 2019046299 A1 | 3/2019 |
| WO | 2019063520 A1 | 4/2019 |
| WO | 2019074938 A1 | 4/2019 |
| WO | 2019102846 A1 | 5/2019 |
| WO | 2019204406 A1 | 10/2019 |
| WO | 2019241659 A1 | 12/2019 |
| WO | 2021052850 A1 | 3/2021 |
| WO | 2021069338 A1 | 4/2021 |
| WO | 2021069343 A1 | 4/2021 |
| WO | 2021197996 A1 | 10/2021 |

OTHER PUBLICATIONS

Ignee; Andre et al, "Ultrasound contrast agents", Endoscopic Ultrasound, Nov.-Dec. 2016, vol. 5, Issue 6, 355-362.

Karani Neerav et al: "Temporal Interpolation of Abdominal MRIs Acquired During Free-Breathing", Sep. 4, 2017 (Sep. 4, 2017), 12th European Conference on Computer Vision, ECCV 2012; [Lecture Notes in Computer Science], Springer Berlin Heidelberg, Berlin, Heidelberg, pp. 359-367, XP047528114, ISSN: 0302-9743 ISBN: 978-3-642-39453-9.

Lusic Hrvoje; et al, "X-Ray Computed Tomography Contrast Agents", Chem. Rev., 2013.

Nouh Mohamed; et al, "Radiographic and magnetic resonances contrast agents: Essentials and tips for safe practices", World Journal of Radiology, Sep. 28, 2017, vol. 9, Issue 9, 339-349.

Qin Chen et al: "Convolutional Recurrent Neural Networks for Dynamic MR Image Reconstruction", IEEE Transactions on Medi-

(56) References Cited

OTHER PUBLICATIONS cal Imaging, IEEE Service Center, Piscataway, NJ, US, Bd. 38, Nr. 1, Jan. 1, 2019 (Jan. 1, 2019), Seiten 280-290, P011694961, ISSN: 0278-0062, DOI: 10.1109/TMI.2018.2863670.
Smits Loek; et al, "Evaluation of ultrasmall superparamagnetic iron oxide (USPIO) enhanced MRI with ferumoxytol to quantify arterial wall inflammation", Atherosclerosis, 2017, 263, 211-218.
Takeshima, Hidenori: "Integrating Spatial and Temporal Correlations into a Deep Neural Network for Low-delay Reconstruction of Highly Undersampled Radial Dynamic Images", International Society for Magnetic Resonance in Medicine, ISMRM, 2030 Addison Street, 7th Floor, Berkeley, CA 94704 USA, pp. 2796, Jun. 1, 2018 (Jun. 1, 2018).
"Written Opinion from PCT Application No. PCT/EP2021/057689", dated Jun. 24, 2021.
Xiao; Yu-Dong et al, "MRI contrast agents: Classification and application (Review)", International Journal of Molecular Medicine, 2016, 38, 1319-1326.
Bellani; Giacomo et al, "Epidemiology, Patterns of Care, and Mortality for Patients With Acute Respiratory Distress Syndrome in Intensive Care Unites in 50 Countries", JAMA, 2016.
Choi; Jun-Ho et al, "EmbraceNet: A robust deep learning architecture for multimodal classification", Information Fusion, 2019, 51, 259-270.
Gong Enhao; et al, "Deep Learning Enables Reduced Gadolinium Dose for Contrast-Enhanced Brain MRI", J. Magn. Reson. Imaging, 2018, 48, 330-340.
"Information on Primovist", 2016.
"International Preliminary Report on Patentability from PCT Application No. PCT/EP2020/077767", dated Apr. 12, 2022.
"Introduction to Multimodal Learning Model", DEV Community, Feb. 5, 2019.
Rajpurkar; Pranav et al, "CheXNet: Radiologist-Level Pneumonia Detection on Chest X-Rays with Deep Learning", 2017.
Yasaka Koichiro; et al, "Deep Learning with Convolutional Neural Network for Differentiation of Liver Masses at Dynamic Contrast-enhanced CT: A Preliminary Study", Radiology, Mar. 2018, vol. 286; No. 3, 887-896.
He, et al., "Deep Predictive Modeling of Dynamic Contrast-Enhanced MRI Data", Proc. Intl. Soc. Mag. Reson. Med., 2019, vol. 27.
Kurozumi, et al., "Evaluation of hemodynamic imaging findings of hypervascular hepatocellular carcinoma: comparison between dynamic contrast-enhanced magnetic resonance imaging using radial volumetric imaging breath-hold examination with k-space-weighted image contrast reconstruction and dynamic computed tomography during hepatic arteriography", Japanese Journal of Radiology, 2018, pp. 295-302, vol. 36.
Zhang, et al., "Dynamic contrast enhanced MR imaging for evaluation of angiogenesis of hepatocellular nodules in liver cirrhosis in N-nitrosodiethylamine induced rat model", Eur. Radiol., 2017, pp. 2086-2094, vol. 27.
Coulden; Richard, "State-of-the-Art Imaging Techniques in Chronic Thromboembolic Pulmonary Hypertension", Proceedings of the American Thoracic Society, 2006, vol. 3, 577-583.
Delcroix Marion; et al, "Chronic Thromboembolic Pulmonary Hypertension; Epidemiology and Risk Factors", Annals of the American Thoracic Society, Jul. 2016, vol. 13 Supp. 13, S201-S206.
"FDA Reclassification Letter regarding OsteoDetect", May 24, 2018.
Galie Nazzareno; et al, "2015 ESC/ERS Guidelines for the diagnosis and treatment of pulmonary hypertension", European Heart Journal, Jan. 2016, vol. 37, Issue 1, 67-119.
Hachulla; et al, "Dual-energy computed tomographic imaging of pulmonary hypertension", Swiss Medical Weekly, 2016, 146; w14328, 1-20.
Smith; Dana, "Artificial Intelligence Can Detect Alzheimer's Disease in Braine Scans Six Years Before a Diagnosis", Jan. 2, 2019.

Tapson Victor; et al, "Incidence and Prevalence of Chronic Thromboembolic Pulmonary Hypertension", Proceedings of the American Thoracic Society, Sep. 7, 2006, vol. 3, 564-567.
Wang; et al, "Stacked Fully Convolutional Networks for Pulmonary Vessel Segmentation", IEEE Visual Communications and Image Processing (VCIP), 2018.
Baccouche; et al, "Sequential Deep Learning for Human Action Recognition", International Workshop on Human Behavior Understanding, 2011, 29-39.
Caraiani; et al, "Description of Focal Liver Lesions With GD-EOB-DTPA Enhanced MRI", Clujul Medical, 2015, vol. 88 No. 4, 438-448.
Chiusano; et al, "DCE-MRI Analysis Using Sparse Adaptive Representations", 2011, 67-74.
Frydrychowicz; et al, "Hepatobiliary MR Imaging with Gadolinium Based Contrast Agents", J Magn Reson Imaging, Mar. 2012, 35 (3), 492-511.
Ghodasara; Satyam et al, "Quantifying Perfusion Properties with DCE-MRI Using a Dictionary Matching Approach", International Society for Magnetic Resonance in Medicine, ISMRM,, Jun. 1, 2018.
"International Preliminary Report on Patentability from PCT Application No. PCT/EP2020/075593", dated Mar. 31, 2022.
"International Preliminary Report on Patentability from PCT Application No. PCT/IB2020/058688", dated Mar. 31, 2022.
"International Search Report and Written Opinion from PCT Application No. PCT/IB2020/058688", dated Dec. 9, 2020.
Ji; et al, "3D Convolutional Neural Networks for Human Action Recognition", IEEE Transactions on Pattern Analysis and Machine Intelligence, Jan. 2013, vol. 35 No. 1, 221-231.
Karpathy; et al, "Large-scale Video Classification with Convolutional Neural Networks", Proceedings of the IEEE Conference on Computer Vision and Pattern Recognition, 2014, 1725-1732.
Khan; et al, "Chapter 3.3 "Neural Networks Basics"", A Guide to Convolutional Neural Networks for Computer Vision, Morgan & Claypool Publishers, 2018, pp. 36-39.
Kim; et al, "Arterial subtraction images of gadoxetate-enhanced MRI improve diagnosis of early-stage hepatocellular carcinoma", Journal of Hepatology, 2019, vol. 71, 534-542.
Kwon; et al, "Differentiation of small (less than or equal to cm) hepatocellular carcinomas from small benign nodules in cirrhotic liver on gadoxetic acid-enhanced and diffusion-weighted magnetic resonance images", Abdominal Imaging, Jul. 6, 2014, pp. 64-78.
Shtern; Alon, "Shape Correspondence Using Spectral Methods and Deep Learning Research Thesis", Aug. 2017.
Simonyan; et al, "Two-Stream Convolutional Networks for Action Recognition in Videos", Advances in Neural Information Processing Systems, 2013, 568-576.
Thompson; et al, "Indicator Transit Time Considered as a Gamma Variate", Circulation Research, Jun. 1964, vol. XIV, 502-515.
Weizman; et al, "Prediction of Brain MR Scans in Longitudinal Tumor Follow-Up Studies", Oct. 1, 2012, pp. 179-187.
"International Preliminary Report on Patentability from PCT Application No. PCT/US2020/021861", dated Sep. 23, 2021.
Bannas; et al, "Combined Gadoxetic Acid and Gadofosveset Enhanced Liver MRI: A Feasibility and Parameter Optimization Study", Magnetic Resonance in Medicine, 2016, 75, 318-328.
Baytas Inci M.; et al, "Patient Subtyping via Time-Aware LSTM Networks", 2017.
Cannella; et al, "Common pitfalls when using the Liver Imaging Reporting and Data System (LI-RADS): lessons learned from a multi-year experience", Abdominal Imaging, Aug. 2, 2018, 43-53.
Conversano; et al, "Hepatic Vessel Segmentation for 3D Planning of Liver Surgery: Experimental Evaluation of a New Fully Automatic Algorithm", Academic Radiology, Apr. 2011, vol. 18/ No. 4, 461-470.
Fischer; et al, "Ultra-high-field imaging of the biliary tract of 7 Tesla: initial results of Gd-EOB-DTPA-enhanced MRCP", Proc. Intl. Soc. Mag. Reson. Med., 2012, 20.
Hope; et al, "Improvement of Gadoxetate Arterial Phase Capture With a High Spatio-Temporal Resolution Multiphase Three-Dimensional SPGR-Dixon Sequence", Journal of Magnetic Resonance Imaging, 2013, 38, 938-945.

(56) References Cited

OTHER PUBLICATIONS

Huang Gao.; et al, "Densely Connected Convolutional Networks", Jan. 28, 2018.

"International Preliminary Report on Patentability from PCT Application No. PCT/EP2020/075288", dated Mar. 31, 2022.

"International Preliminary Report on Patentability from PCT Application No. PCT/EP2020/077775", dated Apr. 12, 2022.

Kim; et al, "Gadoxetic acid-enhanced magnetic resonance imaging: Hepatocellular carcinoma and mimickers", Clinical and Molecular Hepatology, Sep. 2019, vol. 25 No. 3, 223-233.

Knobloch; et al, "Combined Gadoxetic Acid and Gadobenate Dimeglumine Enhanced Liver MRI for Liver Metastasis Detection: A Parameter Optimization Study", Proc. Intl. Soc. Mag. Reson. Med., 2018.

Le; Quoc V., "A Tutorial on Deep Learning Part 2: Autoencoders, Convolutional Neural Networks and Recurrent Neural Networks", Oct. 20, 2015.

Marcan; et al, "Segmentation of hepatic vessels from MRI images for planning of electroporation-based treatments in the liver", Radiol. Oncol., 2014, 48 (3), 267-281.

Meng Qinxue; et al, "Relational Autoencoder for Feature Extraction", Feb. 9, 2018.

Moccia; et al, "Blood vessel segmentation algorithms—Review of methods, datasets and evaluation metrics", Computer Methods and Programs in Biomedicine, 2018, 158, 71-91.

\* cited by examiner

CTEPH.AI Report: CTPA Analysis Report Supporting CTEPH Image Findings

| | |
|---|---|
| Name | John Johnson |
| Date of Birth | 13 October 1962 |
| Patient ID | ID0902348F |
| Accession | 47892347 |
| Study Date | 10 March 2017 2:59pm |

CTEPH.AI is a support tool that provides relevant clinical data as a resource to the clinician and is not intended to be a source of medical advice or to determine or recommend a course of action or treatment for a patient.

CTEPH Findings

Overall pattern of findings is not consistent with CTEPH.

Review the following sections for findings marked with an alert (●). 

 Patient History

| | |
|---|---|
| History of CTEPH | No |
| History of PE | No |
| History of DVT | No |

CTPA History

| CTPA 10 Mar 2019 | N/A | N/A | N/A | N/A |

Cardiovascular Analysis

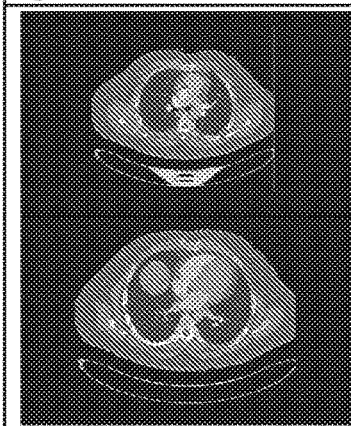

| | |
|---|---|
| RV : LV Diameter Ratio | 0.7 |
| RV : LV Volume Ratio | 1.1 |
| PA Diameter | 7.8 mm |
| PA : aA Ratio | 0.8 |

Lung Parenchymal Attenuation Analysis

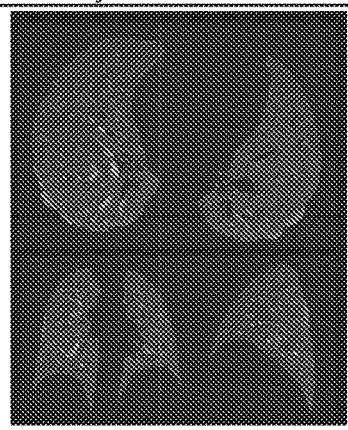

Focal/Asymmetric areas of decreased lung parenchymal attenuation present? No

Chronic Pulmonary Arterial Abnormalities Analysis

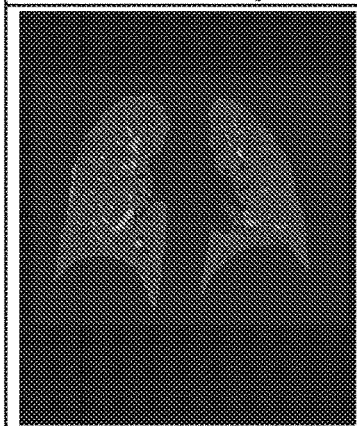

Chronic pulmonary arterial abnormalities present? No

*This analysis does not detect cases of acute PE.*

Scan Quality

 Sufficient Scan Quality

 For the complete information, warnings, and cautions, refer to the Instructions for Use.

Report Generated
10 March 2019 4:14pm
Page 1

FIG. 3B

CTEPH.AI Report: CTPA Analysis Report Supporting CTEPH Image Findings

| | |
|---|---|
| Name | Buck Buckman |
| Date of Birth | 13 May 1970 |
| Patient ID | ID0223348F |
| Accession | 47894522 |
| Study Date | 10 March 2017 2:59pm |

CTEPH.AI is a support tool that provides relevant clinical data as a resource to the clinician and is not intended to be a source of medical advice or to determine or recommend a course of action or treatment for a patient.

CTEPH Findings

There are parameters that could not be analyzed
⊗ Insufficient Scan Quality

Review the following sections for findings marked with an alert (●). 

 Patient History

| | |
|---|---|
| History of CTEPH | No |
| History of PE | No |
| History of DVT | No |

CTPA History

| CTPA 10 Mar 2019 | N/A | N/A | N/A | N/A |
|---|---|---|---|---|

 Cardiovascular Analysis

 Lung Parenchymal Attenuation Analysis

 Chronic Pulmonary Arterial Abnormalities Analysis

Data Unavailable

Data Unavailable

Data Unavailable

Scan Quality

 Insufficient Scan Quality

 For the complete information, warnings, and cautions, refer to the Instructions for Use.

Report Generated
10 March 2019 4:14pm
Page 1

FIG. 3D

SYSTEMS AND METHODS FOR ASSESSING A LIKELIHOOD OF CTEPH AND IDENTIFYING CHARACTERISTICS INDICATIVE THEREOF

CROSS REFERENCE TO RELATED APPLICATION

This application is a U.S. national phase application under 35 U.S.C. § 371 of PCT International Application No. PCT/US2020/021861, filed Mar. 10, 2020, and claims priority to U.S. Provisional Patent Application No. 62/817,295, filed Mar. 12, 2019, the disclosure of which is hereby incorporated by reference in its entirety.

BACKGROUND

Field

The present disclosure relates to systems, methods and software application programs embodying such methods for use in diagnosing chronic thromboembolic pulmonary hypertension (CTEPH) and identifying one or more characteristics indicative thereof within an imaging study of a subject patient.

Description of Related Art

CTEPH is a type of high blood pressure in the arteries of the lungs caused by clots that narrow or block the flow of blood. In most cases of CTEPH, clots in the blood vessels of the legs break off and travel to the lungs. Sometimes, however, blood clots or tissue growth may form in the blood vessels of the lungs. Over time, extra tissue forms over these clots and creates a blockage that cannot be removed with blood-thinner drugs alone.

The median age of patients with CTEPH is 63 years of age, and men and women are equally affected. (See Galiè et al., European Heart Journal, 37-1:67-119, January 2016) The incidence of CTEPH has been difficult to assess and historically has been underestimated. (See Tapson V. F. et al., Proc Am Thorac. Soc. 3-1:564-7 September 2006). The annual incidence of pulmonary embolism (PE) has been estimated at approximately 900,000 cases per year in the United States. (See www.cdc.gov/ncbddd/dvt/data.html (accessed February 2019)) Based on studies after acute PE, 0.57 to 3.8% of those cases may develop CTEPH. (See Delcroix M. et al., Ann Am Thorac. Soc. 13 Suppl. 3:S201-6. July 2016) That projects to an estimated annual incidence of CTEPH of approximately 10 cases per million. Estimates of CTEPH incidence based on registry data, however, suggest an estimated annual incidence of only 5 cases per million. In view of these statistics, it is not surprising that there is low awareness of CTEPH among radiologists.

It typically takes 1.2 to 7 years to diagnose CTEPH in an affected patient, and the current rate of diagnosis of CTEPH is only 13%. The typical (i.e., mean) life expectancy of a patient with CTEPH is less than 3 years if the disease is left untreated. CTEPH is potentially curable by surgery (e.g., pulmonary thromboendarterectomy (PTE)). Riociguat, sold as Adempas® by Bayer, is the only approved treatment in adults with inoperable CTEPH and with persistent/recurrent CTEPH after surgery. In view of the current state of the art, it would be quite advantageous to develop methods and/or systems that would enable CTEPH to be diagnosed earlier than heretofore possible and thus improve the outcomes of patients affected by that disease.

SUMMARY

The present disclosure is directed to systems, methods, and software application programs that can help identify and diagnose the likelihood that a patient is suffering from CTEPH. The systems, methods, and software application programs described herein analyze medical images to detect characteristics of CTEPH and then analyze those characteristics to assess a likelihood that a subject patient is suffering from CTEPH. The novel systems, methods, and software application programs described herein can greatly reduce the time it takes to identify CTEPH, and thereby improve the outcome of patients affected by that disease. Various aspects of the present disclosure may be further characterized by one or more of the following clauses:

Clause 1: A system, comprising: a processor; and a memory storing an application program configured to perform, when executed by the processor, an operation for assessing a likelihood of chronic thromboembolic pulmonary hypertension within a subject patient based upon an analysis of characteristics indicative of chronic thromboembolic pulmonary hypertension within an imaging study of the subject patient, the operation comprising: receiving an initial image set comprising a plurality of images from the imaging study of the subject patient and modifying one or more of the plurality of images from the initial image set to generate a modified image set comprising one or more modified images; identifying from at least one of the modified images of the modified image set one or more characteristics of one or more anatomical structures within a cardiac region of the subject patient indicative of chronic thromboembolic pulmonary hypertension; identifying from at least one of the modified images of the modified image set one or more characteristics of a pulmonary vasculature of the subject patient indicative of chronic thromboembolic pulmonary hypertension; identifying from at least one of the images of the modified image set one or more characteristics of a chronic abnormality in a lung of the subject patient indicative of chronic thromboembolic pulmonary hypertension; and assessing the identified characteristics of the anatomical structures within the cardiac region of the subject patient, the identified characteristics of the pulmonary vasculature of the subject patient, and the identified characteristics of the chronic abnormality in the lung of the subject patient and computing, from this assessment, the likelihood of chronic thromboembolic pulmonary hypertension within the subject patient.

Clause 2: The system of clause 1, wherein the modified image set is generated by an image processing algorithm trained via machine learning to identify, within the plurality of images of the initial image set, images that comprise one or more target organs.

Clause 3: The system of clause 2, wherein the image processing algorithm is further configured to generate one or more of the modified images by cropping one or more images from the initial image set that comprise the one or more target organs to reduce a size of the one or more images from the initial image set.

Clause 4: The system of clause 3, wherein the image processing algorithm is further configured to crop the one or more images from the initial image set by drawing a boundary box around the one or more target organs and removing areas of the image that are outside of the boundary box to reduce the size of the one or more images from the initial image set.

Clause 5: The system of any of clauses 2 to 4, wherein the one or more target organs are the heart and/or lungs.

Clause 6: The system of any of clauses 1 to 5, wherein identifying the one or more characteristics of the one or more anatomical structures within a cardiac region of the subject patient comprises performing, by a first analysis algorithm trained via machine learning, image segmentation on one or more of the modified images to locate the one or more anatomical structures within the one or more modified images.

Clause 7: The system of clause 6, where the one or more anatomical structures comprise at least one of a left ventricle, a right ventricle, a pulmonary aorta, and an ascending aorta.

Clause 8: The system of any of clauses 6 to 7, wherein identifying the one or more characteristics of the one or more anatomical structures within a cardiac region of the subject patient further comprises measuring one or more dimensions of the one or more anatomical structures.

Clause 9: The system of clause 8, wherein the dimensions comprise one or more of a volume of a left ventricle, a radius of the left ventricle, a volume of the right ventricle, a radius of the right ventricle, a volume of the pulmonary aorta, a radius of the pulmonary aorta, a volume of the ascending aorta, and a radius of the ascending aorta.

Clause 10: The system of any of clauses 1 to 9, wherein identifying the one or more characteristics of the pulmonary vasculature of the subject patient comprises identifying, by a second analysis algorithm trained via machine learning, a perfusion abnormality within the one or more modified images.

Clause 11: The system of clause 10, wherein identifying the perfusion abnormality within the one or more modified images comprises analyzing a measured contrast attenuation within a lung parenchyma of the subject patient.

Clause 12: The system of any of clauses 10 to 11, wherein identifying the perfusion abnormality within the one or more modified images comprises: segmenting each of the one or more modified images into voxels; reviewing each voxel to predict whether the voxel is positive or negative for a likelihood of the perfusion abnormality; and aggregating the results of the reviewing step to determine the presence of the perfusion abnormality based at least on part on the proximity of voxels that are positive for the likelihood of the perfusion abnormality relative to one another.

Clause 13: The system of any of clauses 1 to 12, wherein identifying the one or more characteristics of the chronic abnormality in the lung of the subject patient comprises identifying, by a third analysis algorithm trained via machine learning, a vascular abnormality within the one or more modified images.

Clause 14: The system of clause 13, wherein identifying the vascular abnormality within the one or more modified images comprises: segmenting each of the one or more modified images into voxels; reviewing each voxel to predict a risk of the vascular abnormality within the voxel; aggregating the results of the reviewing step to determine a location of voxels predicted to exceed a threshold risk factor; and assessing, based at least in part upon a proximity of voxels determined to exceed the threshold risk factor relative to one another, the presence of the vascular abnormality within the one or more modified images.

Clause 15: The system of any of clauses 13 to 14, wherein identifying the one or more characteristics of the chronic abnormality in the lung of the subject patient further comprises receiving patient information indicative of whether the subject patient has a history of pulmonary embolisms.

Clause 16: The system of any of clauses 13 to 15, wherein the operation further comprises identifying a location of the vascular abnormality and adding a visual indication on one or more of the modified images of the location of the vascular abnormality.

Clause 17: The system of any of clauses 1 to 16, wherein computing the likelihood of chronic thromboembolic pulmonary hypertension within the subject patient comprises using a weighting and scoring algorithm trained via machine learning to generate a confidence weighting for each of the characteristics and computing, using the confidence weightings, an overall score representative of the likelihood of chronic thromboembolic pulmonary hypertension within the subject patient.

Clause 18: The system of any of clauses 1 to 17, wherein the system further comprises a display screen, and wherein the operation further comprises generating a report comprising an indication of the likelihood of chronic thromboembolic pulmonary hypertension within the subject patient and displaying the report on the display screen.

Clause 19: A non-transitory computer-readable storage medium comprising processor-executable instructions with which to perform an operation for assessing a likelihood of chronic thromboembolic pulmonary hypertension within a subject patient based upon an analysis of characteristics indicative of chronic thromboembolic pulmonary hypertension within an imaging study of the subject patient, the operation comprising: receiving an initial image set comprising a plurality of images from the imaging study of the subject patient and modifying one or more of the plurality of images from the initial image set to generate a modified image set comprising one or more modified images; identifying from at least one of the modified images of the modified image set one or more characteristics of one or more anatomical structures within a cardiac region of the subject patient indicative of chronic thromboembolic pulmonary hypertension; identifying from at least one of the modified images of the modified image set one or more characteristics of a pulmonary vasculature of the subject patient indicative of chronic thromboembolic pulmonary hypertension; identifying from at least one of the images of the modified image set one or more characteristics of a chronic abnormality in a lung of the subject patient indicative of chronic thromboembolic pulmonary hypertension; and assessing the identified characteristics of the anatomical structures within the cardiac region of the subject patient, the identified characteristics of the pulmonary vasculature of the subject patient, and the identified characteristics of the chronic abnormality in the lung of the subject patient and computing, from this assessment, the likelihood of chronic thromboembolic pulmonary hypertension within the subject patient.

Clause 20: The non-transitory computer-readable storage medium of clause 19, wherein the modified image set is generated by an image processing algorithm trained via machine learning to identify, within the plurality of images of the initial image set, images that comprise one or more target organs.

Clause 21: The non-transitory computer-readable storage medium of clause 20, wherein the image processing algorithm is further configured to generate one or more of the modified images by cropping one or more images from the initial image set that comprise the one or more target organs to reduce a size of the one or more images from the initial image set.

Clause 22: The non-transitory computer-readable storage medium of clause 21, wherein the image processing algorithm is further configured to crop the one or more images from the initial image set by drawing a boundary box around the one or more target organs and removing areas of the image that are outside of the boundary box to reduce the size of the one or more images from the initial image set.

Clause 23: The non-transitory computer-readable storage medium of any of clauses 20 to 22, wherein the one or more target organs are the heart and/or lungs.

Clause 24: The non-transitory computer-readable storage medium of any of clauses 19 to 23, wherein identifying the one or more characteristics of the one or more anatomical structures within a cardiac region of the subject patient comprises performing, by a first analysis algorithm trained via machine learning, image segmentation on one or more of the modified images to locate the one or more anatomical structures within the one or more modified images.

Clause 25: The non-transitory computer-readable storage medium of clause 24, where the one or more anatomical structures comprise at least one of a left ventricle, a right ventricle, a pulmonary aorta, and an ascending aorta.

Clause 26: The non-transitory computer-readable storage medium of clause 25, wherein identifying the one or more characteristics of the one or more anatomical structures within a cardiac region of the subject patient further comprises measuring one or more dimensions of the one or more anatomical structures.

Clause 27: The non-transitory computer-readable storage medium of clause 26, wherein the dimensions comprise one or more of a volume of a left ventricle, a radius of the left ventricle, a volume of the right ventricle, a radius of the right ventricle, a volume of the pulmonary aorta, a radius of the pulmonary aorta, a volume of the ascending aorta, and a radius of the ascending aorta.

Clause 28: The non-transitory computer-readable storage medium of any of clauses 19 to 27, wherein identifying the one or more characteristics of the pulmonary vasculature of the subject patient comprises identifying, by a second analysis algorithm trained via machine learning, a perfusion abnormality within the one or more modified images.

Clause 29: The non-transitory computer-readable storage medium of clause 28, wherein identifying the perfusion abnormality within the one or more modified images comprises analyzing a measured contrast attenuation within a lung parenchyma of the subject patient.

Clause 30: The non-transitory computer-readable storage medium of any of clauses 28 to 29, wherein identifying the perfusion abnormality within the one or more modified images comprises: segmenting each of the one or more modified images into voxels; reviewing each voxel to predict whether the voxel is positive or negative for a likelihood of the perfusion abnormality; and aggregating the results of the reviewing step to determine the presence of the perfusion abnormality based at least on part on the proximity of voxels that are positive for the likelihood of the perfusion abnormality relative to one another.

Clause 31: The non-transitory computer-readable storage medium of any of clauses 19 to 30, wherein identifying the one or more characteristics of the chronic abnormality in the lung of the subject patient comprises identifying, by a third analysis algorithm trained via machine learning, a vascular abnormality within the one or more modified images.

Clause 32: The non-transitory computer-readable storage medium of clause 31, wherein identifying the vascular abnormality within the one or more modified images comprises: segmenting each of the one or more modified images into voxels; reviewing each voxel to predict a risk of the vascular abnormality within the voxel; aggregating the results of the reviewing step to determine a location of voxels predicted to exceed a threshold risk factor; and assessing, based at least in part upon a proximity of voxels determined to exceed the threshold risk factor relative to one another, the presence of the vascular abnormality within the one or more modified images.

Clause 33: The non-transitory computer-readable storage medium of any of clauses 31 to 32, wherein identifying the one or more characteristics of the chronic abnormality in the lung of the subject patient further comprises receiving patient information indicative of whether the subject patient has a history of pulmonary embolisms.

Clause 34: The non-transitory computer-readable storage medium of any of clauses 31 to 33, wherein the operation further comprises identifying a location of the vascular abnormality and adding a visual indication on one or more of the modified images of the location of the vascular abnormality.

Clause 35: The non-transitory computer-readable storage medium of any of clauses 19 to 34, wherein computing the likelihood of chronic thromboembolic pulmonary hypertension within the subject patient comprises using a weighting and scoring algorithm trained via machine learning to generate a confidence weighting for each of the characteristics and computing, using the confidence weightings, an overall score representative of the likelihood of chronic thromboembolic pulmonary hypertension within the subject patient.

Clause 36: A computer-implemented method for assessing a likelihood of chronic thromboembolic pulmonary hypertension within a subject patient based upon an analysis of characteristics indicative of chronic thromboembolic pulmonary hypertension within an imaging study of the subject patient, comprising: receiving an initial image set comprising a plurality of images from the imaging study of the subject patient and modifying one or more of the plurality of images from the initial image set to generate a modified image set comprising one or more modified images; identifying from at least one of the modified images of the modified image set one or more characteristics of one or more anatomical structures within a cardiac region of the subject patient indicative of chronic thromboembolic pulmonary hypertension; identifying from at least one of the modified images of the modified image set one or more characteristics of a pulmonary vasculature of the subject patient indicative of chronic thromboembolic pulmonary hypertension; identifying from at least one of the images of the modified image set one or more characteristics of a chronic abnormality in a lung of the subject patient indicative of chronic thromboembolic pulmonary hypertension; and assessing the identified characteristics of the anatomical structures within the cardiac region of the subject patient, the identified characteristics of the pulmonary vasculature of the subject patient, and the identified characteristics of the chronic abnormality in the lung of the subject patient and computing, from this assessment, the likelihood of chronic thromboembolic pulmonary hypertension within the subject patient.

Clause 37: The method of clause 36, wherein the modified image set is generated by an image processing algorithm trained via machine learning to identify, within the plurality of images of the initial image set, images that comprise one or more target organs.

Clause 38: The method of clause 37, wherein the image processing algorithm is further configured to generate one or more of the modified images by cropping one or more images from the initial image set that comprise the one or more target organs to reduce a size of the one or more images from the initial image set.

Clause 39: The method of clause 38, wherein the image processing algorithm is further configured to crop the one or more images from the initial image set by drawing a boundary box around the one or more target organs and removing areas of the image that are outside of the boundary box to reduce the size of the one or more images from the initial image set.

Clause 40: The method of any of clauses 37 to 39, wherein the one or more target organs are the heart and/or lungs.

Clause 41: The method of any of clauses 36 to 40, wherein identifying the one or more characteristics of the one or more anatomical structures within a cardiac region of the subject patient comprises performing, by a first analysis algorithm trained via machine learning, image segmentation on one or more of the modified images to locate the one or more anatomical structures within the one or more modified images.

Clause 42: The method of clause 41, where the one or more anatomical structures comprise at least one of a left ventricle, a right ventricle, a pulmonary aorta, and an ascending aorta.

Clause 43: The method of any of clauses 41 to 42, wherein identifying the one or more characteristics of the one or more anatomical structures within a cardiac region of the subject patient further comprises measuring one or more dimensions of the one or more anatomical structures.

Clause 44: The method of clause 43, wherein the dimensions comprise one or more of a volume of a left ventricle, a radius of the left ventricle, a volume of the right ventricle, a radius of the right ventricle, a volume of the pulmonary aorta, a radius of the pulmonary aorta, a volume of the ascending aorta, and a radius of the ascending aorta.

Clause 45: The method of any of clauses 36 to 44, wherein identifying the one or more characteristics of the pulmonary vasculature of the subject patient comprises identifying, by a second analysis algorithm trained via machine learning, a perfusion abnormality within the one or more modified images.

Clause 46: The method of clause 45, wherein identifying the perfusion abnormality within the one or more modified images comprises analyzing a measured contrast attenuation within a lung parenchyma of the subject patient.

Clause 47: The method of any of clauses 45 to 46, wherein identifying the perfusion abnormality within the one or more modified images comprises: segmenting each of the one or more modified images into voxels; reviewing each voxel to predict whether the voxel is positive or negative for a likelihood of the perfusion abnormality; and aggregating the results of the reviewing step to determine the presence of the perfusion abnormality based at least on part on the proximity of voxels that are positive for the likelihood of the perfusion abnormality relative to one another.

Clause 48: The method of any of clauses 36 to 47, wherein identifying the one or more characteristics of the chronic abnormality in the lung of the subject patient comprises identifying, by a third analysis algorithm trained via machine learning, a vascular abnormality within the one or more modified images.

Clause 49: The method of clause 48, wherein identifying the vascular abnormality within the one or more modified images comprises: segmenting each of the one or more modified images into voxels; reviewing each voxel to predict a risk of the vascular abnormality within the voxel; aggregating the results of the reviewing step to determine a location of voxels predicted to exceed a threshold risk factor; and assessing, based at least in part upon a proximity of voxels determined to exceed the threshold risk factor relative to one another, the presence of the vascular abnormality within the one or more modified images.

Clause 50: The method of any of clauses 48 to 49, wherein identifying the one or more characteristics of the chronic abnormality in the lung of the subject patient further comprises receiving patient information indicative of whether the subject patient has a history of pulmonary embolisms.

Clause 51: The method of any of clauses 48 to 50, wherein the method further comprises identifying a location of the vascular abnormality and adding a visual indication on one or more of the modified images of the location of the vascular abnormality.

Clause 52: The method of any of clauses 36 to 51, wherein computing the likelihood of chronic thromboembolic pulmonary hypertension within the subject patient comprises using a weighting and scoring algorithm trained via machine learning to generate a confidence weighting for each of the characteristics and computing, using the confidence weightings, an overall score representative of the likelihood of chronic thromboembolic pulmonary hypertension within the subject patient.

Clause 53: The method of any of clauses 36 to 52, further comprises generating a report comprising an indication of the likelihood of chronic thromboembolic pulmonary hypertension within the subject patient and displaying the report on a display screen.

Clause 54: The method of clause 53, further comprises storing the report in a database.

Clause 55: The method of clause 54, wherein the database is associated with a picture archiving and communication system.

Clause 56: An imaging system, comprising: an imaging modality for performing an imaging study on a subject patient; a hospital information system comprising a database storing information on a medical history of the subject patient; a workstation comprising a display screen; an image processing unit comprising a processor; and a memory storing an application program configured to perform, when executed by the processor, an operation for assessing a likelihood of chronic thromboembolic pulmonary hypertension within the subject patient based upon an analysis of characteristics indicative of chronic thromboembolic pulmonary hypertension within the imaging study of the subject patient, the operation comprising: receiving the initial image set comprising a plurality of images from the imaging study of the subject patient and modifying one or more of the plurality of images from the initial image set to generate a modified image set comprising one or more modified images; identifying from at least one of the modified images of the modified image set one or more characteristics of one or more anatomical structures within a cardiac region of the subject patient indicative of chronic thromboembolic pulmonary hypertension; identifying from at least one of the modified images of the modified image set one or more characteristics of a pulmonary vasculature of the subject patient indicative of chronic thromboembolic pulmonary hypertension; identifying from at least one of the images of the modified image set one or more characteristics of a chronic abnormality in a lung of the subject patient indicative of chronic thromboembolic pulmonary hypertension; and assessing the identified characteristics of the anatomical structures within the cardiac region of the subject patient, the identified characteristics of the pulmonary vasculature of the subject patient, and the identified characteristics of the chronic abnormality in the lung of the subject patient and computing, from this assessment, the likelihood of chronic thromboembolic pulmonary hypertension within the subject patient.

Clause 57: The imaging system of clause 56, wherein the application program is stored in cloud-based memory accessible over a data connection.

BRIEF DESCRIPTION OF THE DRAWINGS

FIG. 3B illustrates another depiction of a display for reporting the results of the systems and methods described herein according to one non-limiting embodiment of the present disclosure;

FIG. 3D illustrates another depiction of a display for reporting the results of the systems and methods described herein according to one non-limiting embodiment of the present disclosure;

DETAILED DESCRIPTION

Figure 1:
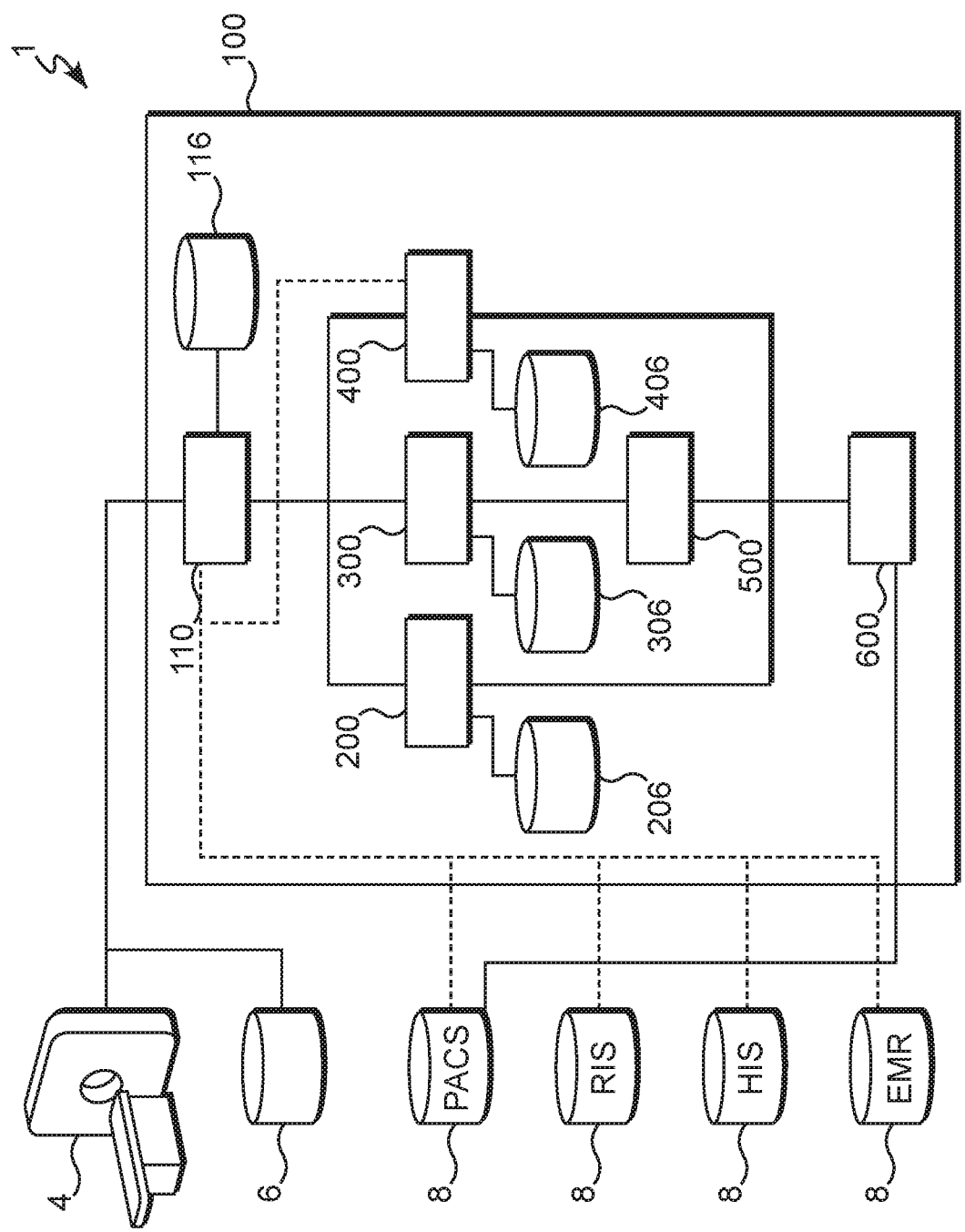
FIG. 1 illustrates an imaging environment and related computing systems according to one non-limiting embodiment of the present disclosure.

For purposes of the description hereinafter, spatial orientation terms shall relate to the embodiment as it is oriented in the drawing figures. However, it is to be understood that the various embodiments of this disclosure may assume alternative variations and step sequences, except where expressly specified to the contrary. It is also to be understood that the specific devices and processes illustrated in the attached drawings, and described in the following specification, are simply exemplary. Hence, specific dimensions and other physical characteristics related to the embodiments disclosed herein are not to be considered as limiting.

As used in the specification, the singular form of "a", "an", and "the" include plural referents unless the context clearly dictates otherwise.

As used herein, the terms "communication" and "communicate" may refer to the reception, receipt, transmission, transfer, provision, and/or the like, of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments, a message may refer to a network packet (e.g., a data packet, and/or the like) that includes data. It will be appreciated that numerous other arrangements are possible.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. As an example, a mobile device may include a cellular phone (e.g., a smartphone or standard cellular phone), a portable computer, a wearable device (e.g., watches, glasses, lenses, clothing, and/or the like), a personal digital assistant (PDA), and/or other like devices. A computing device may also be a desktop computer, server, or other form of non-mobile computer.

As used herein, the term "machine learning algorithm" or "algorithm trained via machine learning" may refer to an algorithm for applying at least one predictive model to a data set. A machine learning algorithm may train at least one predictive model through expansion of the data set by continually or intermittently updating the data set with results of instances of an industrial process. Examples of machine learning algorithms may include supervised and/or unsupervised techniques such as decision trees, gradient boosting, logistic regression, artificial neural networks, convolutional neural networks, Bayesian statistics, learning automata, Hidden Markov Modeling, linear classifiers, quadratic classifiers, association rule learning, or the like. By way of example, a training data set that may be useful for the algorithms described herein can include approximately 6,000 patient cases from various platforms (approximately 200,000 total images) that are then manually annotated by technicians and radiologists.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or sub-ratios beginning with a minimum value of 1 or more and ending with a maximum value of 10 or less, such as but not limited to, 1 to 6.1, 3.5 to 7.8, and 5.5 to 10.

All documents, such as but not limited to issued patents and patent applications, referred to herein, and unless otherwise indicated, are to be considered to be "incorporated by reference" in their entirety.

The present disclosure relates to various aspects of systems, methods, and software application programs embodying processor-executable instructions that can be used to perform an operation for use in the diagnosis of CTEPH and the identification of one or more candidate signs or characteristics indicative thereof within an imaging study of a subject patient. For example, the present disclosure, in certain aspects, pertains to software trained via machine learning for use in applying pattern recognition techniques to an imaging study performed via computed tomography (CT) or other scanning modalities to identify whether one or more characteristics exist in the cardiac region, pulmonary vasculature, and the lungs of a subject patient and to assess an overall likelihood that the identified characteristics collectively constitute a likelihood that the patient suffers from CTEPH. Moreover, while this disclosure focuses on CTEPH, the concepts described herein are not limited to CTEPH and could find application in the analysis of other medical conditions and/or diseases, especially those which can be identified or diagnosed through the identification of various characteristics that can be recognized from an analysis of medical images.

The systems and methods described herein are implemented as a set of software modules or units that work together to analyze computed tomography pulmonary angiogram (CTPA) images acquired from computed tomography (CT) imaging modalities (e.g., scanners) and provide individual and consolidated output indicating whether the analyzed images have indications of CTEPH. With reference to FIG. 1, system 1 can include a software set 100 that includes a pre-processor module 110, a cardiovascular measurement analysis (CMA) module 200, a lung parenchymal attenuation (LPA) module 300, a chronic pulmonary arterial abnormalities (CPAA) module 400, a supervisory classifier module 500, and a post-processor module 600. The various modules can be in the form of an application program comprised of programming instructions stored in non-transitory, computer-readable media that can be executed by a processor to perform the steps, methods, or processes provided for in the instructions. The application program can be stored locally, such as in memory on a server or other hardware item (e.g., in a CT scanner or injector or on a server) or they can be stored in a cloud-based or other distributed arrangement whereby multiple clients can access the program over a data connection and execute the application program simultaneously. The lines in FIG. 1 depict typical lines of communication between the various elements according to certain non-limiting embodiments of the present disclosure. Certain lines are depicted in dashed format to show communication of patient information (e.g., medical history, procedure history) from and to, for example, the various information sources 8 described herein.

Figure 2:
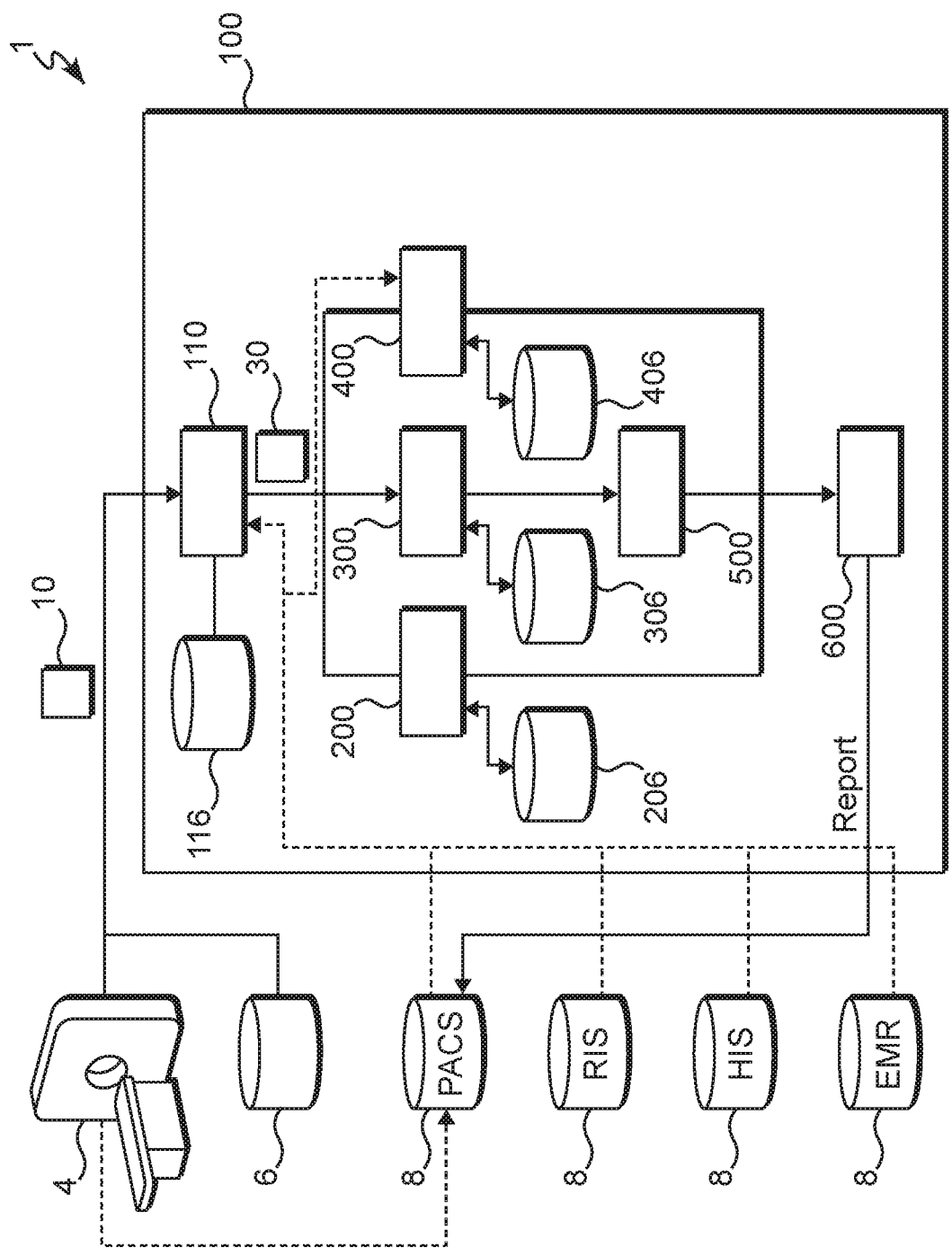
FIG. 2 illustrates a diagram of a system workflow in the imaging environment of FIG. 1 according to one non-limiting embodiment of the present disclosure.

FIG. 2 depicts system 1 of FIG. 1 with the lines and arrows depicting a flow of information according to certain non-limiting embodiments of the present disclosure. With reference to FIG. 2, an initial image set 10, such as a set of CT images (e.g., a set of CTPA images), can be obtained from a medical imaging modality 4, such as a CT scanner, or from a database 6 where images from prior imaging studies are stored. Initial image set 10 may contain over 300 images. CT scanners and CT images are well known in the art. While this disclosure focuses on CT images, the concepts described herein are not limited to only the analysis of CT images and could find application in the analysis of other medical images, such as for example, MRI images.

Pre-Processor Module

With continued reference to FIG. 2, initial image set 10 can be received by pre-processor module 110. Initial image set 10 may include images (slices) of multiple organs as well as the surrounding background. Since much of this information is not needed to perform the analysis discussed herein, and retaining this information as part of the initial image set 10 can lead to long processing times and may exceed available memory, pre-processor module 110 can provide a modified set of images that is cropped so as to contain only those organs (or portions thereof) that are needed for the downstream analysis. Pre-processor module 110 can be configured to crop the images from initial image set 10 in order to narrow the images contained in initial image set 10 to particular images (and/or portions thereof) that can be passed through the remainder of software set 100. In some non-limiting embodiments, pre-processor module 110 can apply 3D-image processing techniques to locate the target organs, such as the lungs and/or heart. Once the target organs are located, pre-processor module 110 can draw a reliable bounding box around the organ(s) and crop the image(s) such that only that contained within the bounding box remains as part of the image, thereby reducing the size of the image files. Pre-processor module 110 can also discard or ignore any images that do not contain the target organ, or that contain only an obstructed view of the target organ. The output of pre-processor module 110 can be a modified image set 30 which has been derived from the initial image set 10.

In certain non-limiting embodiments, the process of locating and bounding the target organs performed by pre-processor module 110 can be performed with an algorithm trained via machine learning. This machine learning can involve use of a training set comprised of CT or other image sets (e.g., 5,000 CTPA images) that have been annotated by radiologists and/or technologists to identify one or more target organs, such as the lungs and heart. The machine learning may include generating predictive models based on these annotated images. The predictive models may predict an expected location, size, and shape of the target organs and train the pre-processor module 110 to locate these organs and to draw an accurate and reliable bounding box around the organs that can be used to prepare the modified images. The predictive models may be generated using interpolations of existing data, database lookups of matches, multiple regression models, or any number of machine learning and neural network techniques and algorithms, such as the machine learning algorithms mentioned above. By way of further example, image segmentation can be performed by U-Net, which is a convolutional neural network developed for biomedical image segmentation at the Computer Science Department of the University of Freiburg, Germany. Alternatively, a sliding-window convolutional network can be used.

Pre-processor module 110 can also convert the format of the images. For example, while the images in initial image set 10 may be DICOM images, if a different image format (e.g., NIFTI format) is utilized by other modules in software set 100, pre-processor module 110 can convert the images to the desired format either before, during, or after the modified image set 30 is generated.

Pre-processor module 110 can additionally be in communication with various patient information sources 8. Information sources can include registries, repositories, and reporting systems which are commonly associated with medical imaging. These include picture archiving and communication systems (PACS), radiology information systems (RIS), hospital information systems (HIS), electronic medical record (EMR) systems, and similar systems and data repositories. These sources typically contain information in the form of images, imaging reports, patient demographics, patient medical history, etc. Pre-processor module 110 can search for and retrieve from these systems relevant information about a patient that may assist in the analysis to be completed by system 1. For example, for identifying one or more characteristics indicative of CTEPH in a patient, pre-processor module 110 may determine if the patient has a history of pulmonary embolisms, CTEPH, and/or deep vein thrombosis. Information about the patient's history can be condensed into flags (e.g., binary indications of whether the patient has a history of certain conditions) that can be passed to other modules in software set 100. Rather than searching existing systems for this information, pre-processor module 110 (or any other component of system 1) can prompt a user to provide this information, such as through a user interface associated with system 1 and/or pre-processor module 110.

Modified image set 30 can be stored in a database, such as a database 116 associated with pre-processor module 110, and/or communicated to other modules in software set 100, such as each of the CMA module 200, LPA module 300, and CPAA module 400. The design and operation of each of these modules will be described, in turn, below. The particular order of this description should not be viewed as limiting and each module can generally operate simultaneously or sequentially with any other module, as will be appreciated through the description below.

Cardiovascular Measurement Analysis (CMA) Module

CMA module 200 can be configured to receive modified image set 30, identify one or more anatomical structures of interest within the one or more modified images, and measure one or more characteristics of the one or more anatomical structures. By way of further example, CMA module 200 can identify and measure the cardiovascular anatomy, such as cardiac and/or lung structures that appear in the one or more images, examples of which include the left and right ventricles, the ascending aorta, and the pulmonary artery. Additional detail concerning the design and operation of the CMA module 200 are provided below.

With reference to FIG. 2, CMA module 200 can receive an image set, such as modified image set 30. These images can be received from, for example, pre-processor module 110. The images may also be retrieved from a database, such as a database 116 associated with pre-processor module 110 where such images have been stored.

Upon receipt, images, such as modified images 30, can optionally be resized and checked to ensure sufficient contrast enhancement exists in the images. If sufficient enhancement does not exist, CMA module 200 can report this issue to pre-processor module 110 and/or elsewhere in system 1 so that the new images can be obtained.

Image segmentation can then be performed on the images to identify, within the images, anatomical areas of interest within the one or more cropped images, such as certain anatomical structures of the heart and/or lungs. Segmentation can be performed automatically with an algorithm trained via machine learning. This machine learning can involve the use of a training set comprised of images of the heart and lungs that have been annotated by radiologists and/or technologists to identify the structures in the heart and lungs, such as the left and right ventricles, the ascending aorta, and the pulmonary artery. The machine learning may include generating predictive models based on these annotated images. The predictive models may predict an expected location, size, and shape of the structures in the heart and lungs. The predictive models may be generated using interpolations of existing data, database lookups of matches, multiple regression models, or any number of machine learning and neural network techniques and algorithms, such as the machine learning algorithms mentioned above.

For example, image segmentation can involve first generating 3-D objects from 2-D CTPA slices. From the 3-D object, the heart region can be localized, such as through a 2-D convolutional neural network (CNN) algorithm trained through deep learning. Segmentation of the cardiac structures can be completed by a 3-D CNN algorithm trained through deep learning.

Once segmentation is complete and certain structures of the heart and lungs have been identified within one or more images, CMA module 200 can automatically measure the structures to determine their size and/or dimensions. The measurement process can include a review of multiple images from modified image set 30 to determine the optimal angle to perform the measurement, where the optimal angle is one which provides an unobstructed view of the structure and accurate perspective of the structure's size and shape relative to its surroundings. CMA module 200 can employ known image measurement techniques, non-limiting examples of which include the centerline method and the sphere-fitting method. While the measurements that can be performed by CMA module 200 are not limited, certain measurements, described below, can assist in the identification of CTEPH according to the methods described herein.

For example, CMA module 200 may perform a left ventricle measurement to measure the size (e.g., radius, diameter, and/or volume) of the left ventricle, which is the main pumping chamber of the heart, responsible for pumping oxygen-rich blood to the entire body. CMA module 200 may also perform an ascending aorta measurement to measure the size (e.g., radius, diameter, and/or volume) of the ascending aorta, which is the first section of the aorta starting from the left ventricle and extending to the aortic arch. CMA module 200 may additionally perform a pulmonary artery measurement to measure the size (e.g., radius, diameter, and/or volume) of the pulmonary artery, which is the artery carrying blood from the right ventricle of the heart to the lungs for oxygenation. By way of further example, CMA module 200 may perform a right ventricle measurement to measure the size (e.g., radius, diameter, and/or volume) of the right ventricle, which is the chamber of the heart responsible for pumping oxygen-depleted blood to the lungs. By way of further example, CMA module 200 may measure the degree of curvature of a septum.

Once the measurements are obtained, CMA module 200 may compute comparisons or ratios of the measured values. Non-limiting examples include the ratio of the volume of the left ventricle to the volume of the right ventricle (LV:RV volume); the ratio of the volume of the pulmonary aorta to the volume of the ascending aorta (PA:AA volume); the ratio of the radius of the left ventricle to the radius of the right ventricle (LV:RV radius); and the ratio of the radius of the pulmonary aorta to the radius of the ascending aorta (PA:AA radius). Alternatively, these ratios can be calculated elsewhere in system 1, such as by supervisory classifier module 500, which is discussed below.

These measurements and/or computed ratio values can be stored by CMA module 200, such as in a database 206 associated with CMA module 200, where they are associated with the particular image set for which they relate. CMA module 200 may also communicate some or all of these values to other modules within, or external to, system 1, such as supervisory classifier module 500.

CTEPH causes abnormalities in the pulmonary vessels, increasing their resistance to flow and typically results in pulmonary hypertension and right ventricle strain. Pulmonary hypertension causes the right ventricle to work harder and results in right ventricular dilation, out of proportion to the left ventricle. It has been found that the ratios discussed above can serve as characteristics indicative of the presence of CTEPH. For example, a study of the LV:RV volume in normal patients versus patients suffering from pulmonary hypertension (e.g., cases diagnosed as CTEPH, pulmonary embolism, lung disease, or other chronic pulmonary hypertension disease) showed that the LV:RV volume was typically more asymmetrical (i.e., not 1:1) and skewed toward a larger RV volume for the pulmonary hypertension patients. Conversely, the LV:RV radius and the PA:AA radius tended to be more symmetrical for pulmonary hypertension patients than for normal patients. From the results of this study, a support vector machine classifier (SVC) (with a linear kernel to avoid overfitting) could be employed to analyze separability of the classes based on the measured features so as to predict from these measurements characteristics of these anatomical structures that are indicative of pulmonary hypertension, and hence CTEPH.

Lung Parenchymal Attenuation (LPA) Module

LPA module 300 can be configured to receive modified image set 30 (which can be the same image set provided to CMA module 200) and determine from these images one or more characteristics of the pulmonary vasculature that is shown in the images. Additional details concerning the design and operation of the LPA analysis module 300 are provided below.

With reference to FIG. 2, LPA analysis module 300 can receive an image set, such as modified image set 30. These images can be received from, for example, pre-processor module 110. The images may also be retrieved from a database, such as a database 116 associated with pre-processor module 110 where such images have been stored.

Upon receipt of the images, the modified images 30 can optionally be resized and checked to ensure sufficient contrast enhancement exists in the images. If sufficient enhancement does not exist, LPA module 300 can report this issue to pre-processor module 110 and/or elsewhere in system 1 so that the new images can be obtained. Image segmentation can be performed on the images, though segmentation is not required. If performed, segmentation may be used to segment the images, such as into a series of voxels, by tissue type. LPA module 300 can also perform a fully automated segmentation of the lung vessels. This can include extracting the vessel topography to individually assign voxels to their corresponding vessels and calculating a 3-D representation of the vessel to potentially detect occlusions or cut-off vessels.

LPA module 300 can then analyze the cropped images (with or without segmentation) to identify one or more characteristics of the pulmonary vasculature.

In one non-limiting embodiment, the one or more characteristics of the pulmonary vasculature identified by LPA module 300 include whether or not there are geographic changes in the lung parenchyma that are suggestive of a perfusion abnormality. This identification may be based upon a review and analysis of the measured contrast attenuation at a particular location within the lung parenchyma. The presence of focal/asymmetric areas of decreased lung parenchymal contrast attenuation observed in the images may be indicative of perfusion, such as due to a decreased vessel count. Vascular abnormalities can result in perfusion abnormalities. Sharply demarcated areas of attenuation mixed with areas of normal lung attenuation, sometimes referred to as a "mosaic attenuation pattern," is frequently seen with CTEPH, but may be a nonspecific feature.

In other non-limiting embodiments, the one or more characteristics of the pulmonary vasculature identified by LPA module 300 may include a volume of a stenosis of one or more pulmonary vessels, a degree of irregularity of one or more pulmonary vessels, a minimum diameter of one or more pulmonary vessels, a quantitative flow reserve (QFR) of one or more pulmonary vessels and a location and a severity of at least one of the stenosis, the degree of irregularity, the minimum diameter and the quantitative flow reserve.

The analysis by LPA module 300 can be completed on one image at a time by using a sliding window algorithm to review each segmented voxel (e.g., cube or brick) and predict whether the particular voxel of the image is positive or negative for a perfusion abnormality. The results of the review can be aggregated, and the aggregated results can be reviewed to determine if the image is indicative of a perfusion abnormality. In one non-limiting embodiment, the presence of multiple at-risk voxels is deemed to be indicative of a perfusion abnormality.

The analysis performed by LPA module 300 can be performed automatically with an algorithm trained via machine learning. This machine learning can involve the use of a training set comprised of images of the lungs that have been annotated by radiologists and/or technologists to identify one or more characteristics of the pulmonary vasculature, such as one or more characteristics indicative of a perfusion abnormality. The machine learning may include generating predictive models based on these annotated images. The predictive models may predict an expected pattern or value of contrast attenuation that is indicative of perfusion. The predictive models may be generated using interpolations of existing data, database lookups of matches, multiple regression models, or any number of machine learning and neural network techniques and algorithms, such as the machine learning algorithms mentioned above. As an alternative to training the algorithm through manually annotated images, vascular tree masks generated by conventional image processing algorithms could serve as input to train a 3D segmentation network.

The results of the image analysis performed by LPA module 300 can be stored by LPA module 300, such as in a database 306 associated with LPA module 300, where they are associated with the particular image set for which they relate. LPA module 300 may also communicate some or all of these results to other modules within, or external to, system 1, such as supervisory classifier module 500. In one non-limiting example, the results of the image analysis performed by LPA module 300 that are stored and/or communicated can be denoted as a binary (e.g., "yes" or "no") value identifying whether or not indicators of perfusion were detected. For example, if LPA module 300 detected the presence of focal/asymmetric areas of decreased lung parenchymal contrast attenuation, LPA module 300 can generate a "yes" flag identifying the image set as containing evidence of perfusion.

Chronic Pulmonary Arterial Abnormalities (CPAA) Module

CPAA module 400 can be configured to receive modified image set 30 and identify whether one or more characteristics of a chronic abnormality in the lungs appear in the images. By way of further example, CPAA module 400 can identify one or more chronic abnormalities in the pulmonary vessels, such as arterial abnormalities like cut-off, wall thickening, webs, bands, and/or other disorders such as mottled perfusion or focal differences in the lung that are suggestive of CTEPH. CPAA module 400 may also be configured to visually flag the abnormality, such as by drawing a box or circle around the abnormality, on one or more images from modified image set 30.

Chronic intraluminal thrombus can cause a complete obstruction, also referred to as cut-off vessels, or there may be peripheral migration and adherence of the organized thrombus to the vessel wall, resulting in smooth or sometimes nodular thickening of the wall. Incomplete recanalization of a previously occluded artery gives rise to bands, webs, and stenosis, which may be accompanied by post-stenotic dilation.

With reference to FIG. 2, CPAA module 400 can receive an image set, such as modified image set 30. These images can be received from, for example, pre-processor module 110. The images may also be retrieved from a database, such as a database 116 associated with pre-processor module 110 where such images have been stored.

Upon receipt of the images, the images of modified image set 30 can optionally be resized and checked to ensure sufficient contrast enhancement exists in the images. If sufficient enhancement does not exist, CPAA module 400 can report this issue to pre-processor module 110 and/or elsewhere in system 1 so that the new images can be obtained. Once the images are received, CPAA module 400 can also perform additional image processing. For example, because the abnormalities detected in this step are relatively small in size, steps can be taken to make the abnormalities easier to differentiate and identify. In one non-limiting embodiment, a sliding window algorithm can be run to break down one or more of the images into smaller voxels (e.g., cubes) of limited pixel size, such as voxels on the order of 128×128×50 pixels.

The analysis performed by CPAA module 400 can then proceed on a voxel-by-voxel basis over the relevant area or over the entire image to predict, for each voxel, the risk that a vascular abnormality is contained within that voxel. For example, a classifier, such as a 3-class-cube-level classifier, can be employed to predict whether or not a cube exhibits a risk of chronic pathology. In certain non-limiting embodiments, the classifier can make this prediction by assigning a trained risk weight to each voxel. For instance, a voxel, once analyzed, can be labeled as "normal" or "no risk" or it can be assigned a score ranging from 1-4, where 1 indicates a "low risk" and 4 indicates a "high risk" that a vascular abnormality appears in the voxel.

Once the CPAA module 400 has assessed the risk in each voxel (or at least a sufficient number of voxels), the location of the at-risk voxels relative to one another can be assessed to determine whether, due to the proximity of at-risk voxels, there is a likelihood of the existence of a vascular abnormality. For example, if a threshold number of adjacent voxels (e.g., 2, 3, or 4) each exhibits a threshold risk (e.g., a risk score of 2, 3, or 4) of vascular abnormality, CPAA module 400 can identify those voxels as representing the location of a likely abnormality.

CPAA module 400 can also receive patient-specific information that can be used to assess the risk of a vascular abnormality in the modified image set 30. For example, CPAA module 400 can receive the information discussed above in connection with the pre-processor module 110, including information on whether the patient has a history of pulmonary embolisms, CTEPH, or deep vein thrombosis. This information can be received from one or more information sources 8, for example, the electronic medical record (EMR) system, it can be input to CPAA module 400 by an operator through a user interface associated with system 1 or with CPAA module 400, or it can be derived from the medical history flag applied by the pre-processor module 110 discussed above.

Patient history can be applied by CPAA module 400 in setting the threshold for what constitutes a "risk" that a particular voxel, or for a collection of voxels, exhibits a vascular abnormality. This threshold can be adjusted upward (making it less likely that a voxel will be considered "at-risk") or downward (making it more likely that a voxel will be considered "at-risk") based on the patient history. Alternatively, the patient history can be considered along with the fraction of voxels exhibiting a certain risk level to predict a likelihood that a chronic abnormality exists at a certain location, with the presence of a history of, for example, pulmonary embolisms decreasing the number of "at-risk" voxels that are required before the patient is identified as exhibiting a chronic vascular abnormality. A patient's history, and particularly a patient's history with pulmonary embolisms, has been found to be an indicator of the likelihood that a vascular abnormality will exist, so use of this information to adjust the threshold for the risk determination can result in a more accurate assessment of a patient's overall risk of CTEPH.

As mentioned, once an abnormality is identified, CPAA module 400 can visually flag the abnormality, such as by drawing a box or circle around the abnormality, on one or more images from modified image set 30. This can be accomplished by identifying the location of the at-risk voxels and editing the image file to provide a visual cue or annotation (e.g., a box) around the at-risk voxels along with a certain buffer area outside of the at-risk voxels to capture the periphery of the abnormality. Once the abnormality is "drawn" on the image file, the revised image file can be saved in a database (e.g., database 406 associated with CPAA module 400) and/or communicated to other modules (e.g., post-processing module 600) in system 1.

The above process represents one non-limiting embodiment for identifying one or more chronic abnormalities. Other processes that achieve this result are also within the scope of this disclosure, including processes that do not include breaking down the images into smaller voxels and processes that do not include assessing risk using a trained weight score.

The results of the image analysis performed by CPAA module 400 can be stored by CPAA module 400, such as in a database 406 associated with CPAA module 400, where they are associated with the particular image set for which they relate. CPAA module 400 may also communicate some or all of these results to other modules within, or external to, system 1, such as supervisory classifier module 500 and/or post-processing module 600. Included among the results can be the binary (e.g., "yes" or "no") value identifying whether or not a chronic abnormality was detected as well as a copy of one or more images with the abnormality visually identified with, for example, a box or circle drawn around it.

The identification process can be performed automatically with an algorithm trained via machine learning. This machine learning can involve use of a training set comprised of images of the lungs that have been annotated by radiologists and/or technologists to identify one or more chronic abnormalities, such as one or more chronic abnormalities in the pulmonary vessels. The machine learning may include generating predictive models based on these annotated images. The predictive models may predict an expected location, size, and shape of the abnormalities. The predictive models may be generated using interpolations of existing data, database lookups of matches, multiple regression models, or any number of machine learning and neural network techniques and algorithms, such as the machine learning algorithms mentioned above.

Supervisory Classifier Module

Supervisory classifier module 500 can be configured to receive and aggregate the outputs of the CMA module 200, the LPA module 300, and/or the CPAA module 400. In a preferred embodiment, outputs from all of the CMA module 200, the LPA module 300, and the CPAA module 400 are received by supervisory classifier module 500. To the extent these outputs are received at different times due to asynchronous processing of data in the other modules, supervisory classifier module 500 can cache the outputs until all expected data has arrived. Once all necessary and/or expected outputs and other data has been received by supervisory classifier module 500, supervisory classifier module 500 can analyze the information to determine if the information is, or is not, indicative of a risk of CTEPH.

For example, supervisory classifier module 500 can be configured as a neural network-based module that is devised by combining multiple outputs for the diagnosis of CTEPH. The output of supervisory classifier module 500 can be based on the inputs provided to it in the form of the predictions of the LPA module 300 and CPAA module 400 as well as the measurements provided by CMA module 200 and patient information, such as a patient's medical history with pulmonary embolisms, CTEPH, and/or deep vein thrombosis. The output can be in the form of a binary (yes/no) indication of whether the overall findings are indicative of CTEPH.

By way of further example, supervisory classifier module 500 can use at least one weighting and scoring algorithm for use in determining a confidence weighting for each of the candidate abnormalities identified by the CMA module 200, LPA module 300, and CPAA module 400 as existing in the cardiac region, the pulmonary vasculature, and the lungs, respectively, and computing, using the confidence weightings, an overall score representative of a likelihood that the identified candidate abnormalities collectively constitute a likelihood of CTEPH. This score can be compared to a threshold value and, if the score exceeds the threshold value, supervisory classifier module 500 can determine that the patient is suffering from CTEPH.

The diagnosis process of supervisory classifier module 500 can be performed with an algorithm trained through machine learning. This machine learning can involve use of a training set comprised of studies that have been determined by radiologists and/or technologists to be either negative for CTEPH or positive for CTEPH. The machine learning may include generating predictive models based on these study results and the known characteristics about the patients who were the subject of these studies, including whether the patients had or did not have the characteristics measured and/or detected by CMA module 200, the LPA module 300, and/or the CPAA module 400. The predictive models may predict whether, based on available information, a patient is likely to have CTEPH. The predictive models may be generated using interpolations of existing data, database lookups of matches, multiple regression models, or any number of machine learning and neural network techniques and algorithms, such as the machine learning algorithms mentioned above. It is noted that the training used in training each of the CMA module 200, LPA module 300, CPAA module 400, and supervisory classifier module 500 may be the same training set or a different training set used in training one or more of the other modules. In other words, the same training set may (or may not) be used to train more than one of the CMA module 200, LPA module 300, CPAA module 400, and supervisory classifier module 500. The results generated from any aspect of software set 100 can be used to further train and refine the modules described herein.

Post-Processor Module

Post-processor module 600 can be configured to format data generated by software set 100, including some or all of the outputs from the various modules in software set 100, into a format for report generation. For example, post-processor module 600 can be configured to extract images from the modified image set 30 and/or images that have been annotated by CPAA module 400 to identify a potential abnormality and include those images in a report for the subject patient or subject CTPA study. Post-processor module 600 can also be configured to draw the regions of interest identified by CPAA module 400 (e.g., the abnormalities) based upon information provided by CPAA module 400 to the extent that CPAA module 400 did not generate images that contain such annotations. In addition, post-processor module 600 can format and summarize the findings of software set 100 into an easy to consume format for report generation. Post-processing module 600 can also identify any errors or information that is missing from the data set.

Figure 3A:
FIG. 3A illustrates one depiction of a display for reporting the results of the systems and methods described herein according to one non-limiting embodiment of the present disclosure.
Figure 3C:
FIG. 3C illustrates another depiction of a display for reporting the results of the systems and methods described herein according to one non-limiting embodiment of the present disclosure.

Exemplary reports that can be generated by post-processing module 600 are shown in FIGS. 3A-3D. In each report, patient information, such as name, age, study date, and patient history, is provided, and such information can be derived from information in the EMR or other appropriate source. The reports of FIGS. 3A-3B also include and summarize the ultimate finding of supervisory classifier module 500 under "CTEPH Findings." In FIG. 3A, for instance, the supervisory classifier module 500 determined from the available information that the overall pattern of findings is indicative of CTEPH while, in FIG. 3B, the supervisory classifier module 500 determined from the available information that the overall pattern of findings is not consistent with CTEPH. In the report of FIGS. 3A-3B, the results of each of the CMA module 200, LPA module 300, and CPAA module 400 are reported separately. However, in the reports of FIGS. 3C-3D, the output of at least one of the modules was unavailable. In the reports of FIGS. 3C-3D, the supervisory classifier module 500 was unable to provide a CTEPH assessment due to this missing information.

The report format of FIGS. 3A-3D is exemplary only, and reports of other formats and styles can be generated by post-processing module 600. It is contemplated that the style of report can be customized by each user and/or organization through configuration tools associated with post-processing module 600. The reports generated by post-processing module 600 or from the formatted data provided by post-processing module 600 can be visually displayed on a display screen, such as a display screen of a workstation used by radiologists or other medical personnel.

Figure 4:
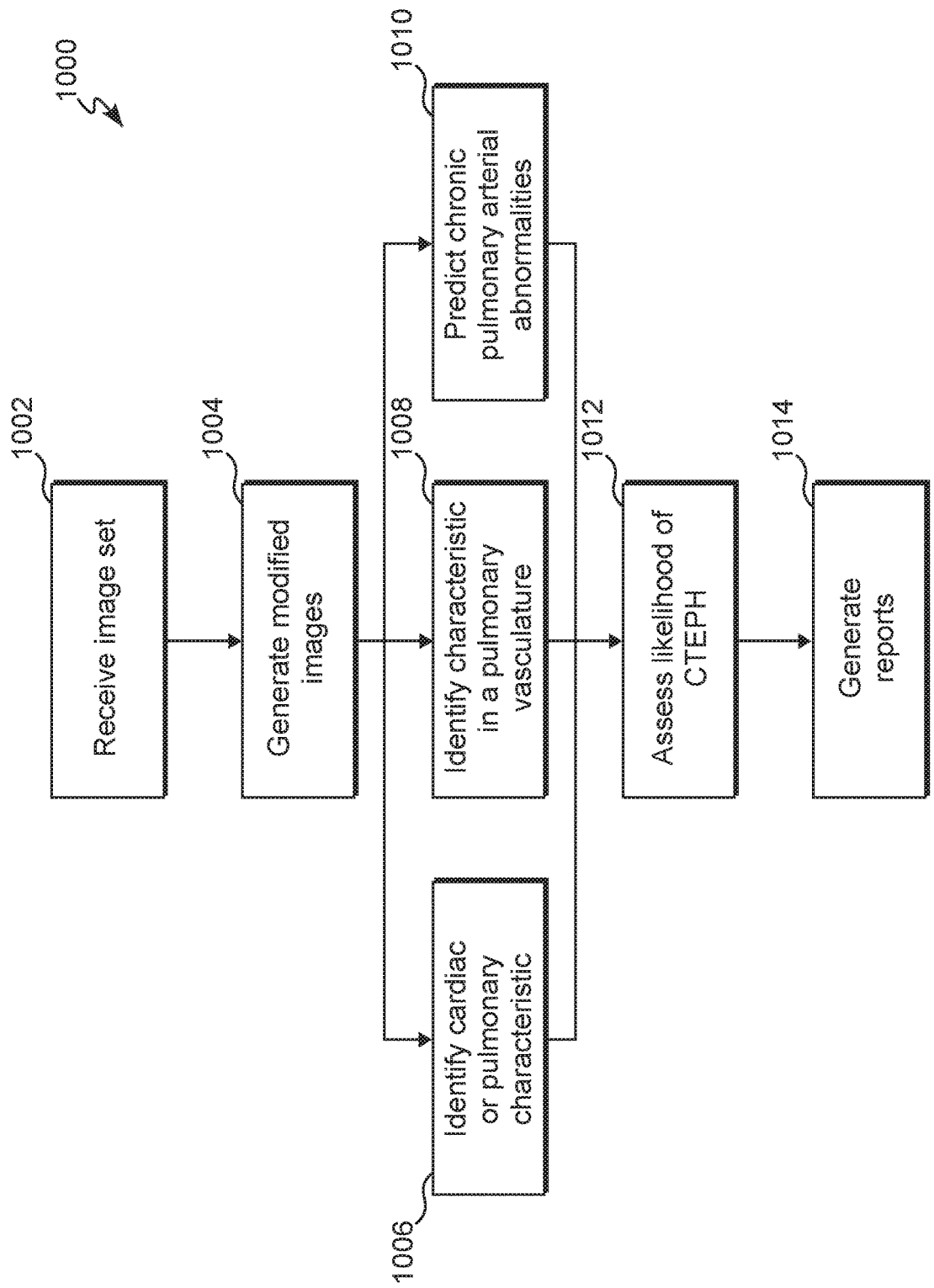
FIG. 4 illustrates a flow diagram of a method according to one non-limiting embodiment of the present disclosure.

Referring to FIG. 4, a method 1000 is shown for identifying one or more characteristics signs indicative of CTEPH within an imaging study of a subject patient according to certain non-limiting embodiments. The method can be implemented by system 1 and software set 100, and generally follows the work flow described above.

With continued reference to FIG. 4, step 1002 may include receiving at least one image set from an imaging study performed on the subject patient.

With continued reference to FIG. 4, step 1004 may include modifying the image set to generate a modified image set 30, depicted here as a set of cropped images. Examples of this process are described in connection with the pre-processing module 110 described above.

With continued reference to FIG. 4, step 1006 may include using the modified image set 30 to identify at least one characteristic in a cardiac or pulmonary region of the subject patient. Examples of this process are described in connection with the CMA module 200 described above, and can include segmenting one or more of the cropped images to locate anatomical structures of the heart or lungs, measuring those structures, and computing ratios of those measurements.

With continued reference to FIG. 4, step 1008 may include using the modified image set 30 to identify at least one characteristic in a pulmonary vasculature of the subject patient. Examples of this process are described in connection with the LPA module 300 above, and can include analyzing the lung parenchymal contrast attenuation for evidence of a perfusion.

With continued reference to FIG. 4, step 1010 may include analyzing the modified image set 30 to predict the presence and/or absence of chronic pulmonary arterial abnormalities in the subject patient. Examples of this process are described in connection with the CPAA module 400 described above, and can include segmenting the image into voxels (e.g., cubes), predicting the risk each voxel exhibits a chronic abnormality, assessing the overall likelihood and location of the vascular abnormality, and visually identifying on one or more images the location of the abnormality.

With continued reference to FIG. 4, step 1012 may include analyzing the outputs of the various modules of software set 100 to assess whether the outputs are indicative of CTEPH. Examples of this process are described in connection with the supervisory classifier module 500 described above, and can include predicting the risk that the subject patient has CTEPH.

With continued reference to FIG. 4, step 1014 may include generating a report from the outputs of the various modules of software set 100. Examples of this process are described in connection with the post-processor module 600 described above, and can include formatting the data into a report that can be displayed on a display screen.

While method 1000 is described as a series of steps, the steps need not be performed sequentially. For example, steps 1006, 1008, and 1010 can be performed sequentially or simultaneously. However, typically step 1002 should precede step 1004; step 1004 should precede steps 1006, 1008, and 1010; step 1012 should follow steps 1006, 1008, and 1010; and step 1014 should follow step 1012.

Figure 5:
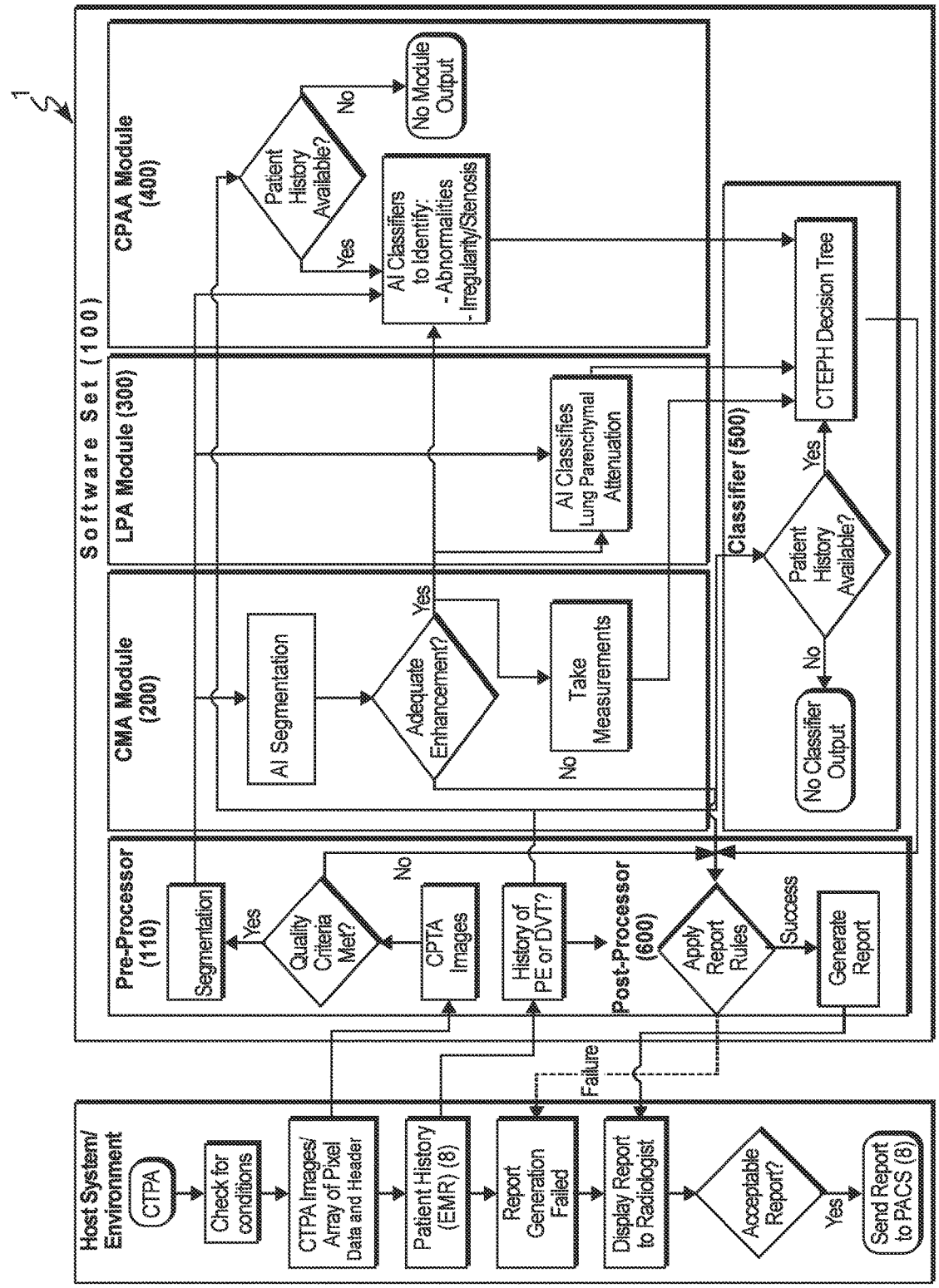
FIG. 5 is a flow chart of the work flow of the software application program of the present disclosure according to one non-limiting embodiment of the present disclosure.

FIG. 5 is a flow chart of the work flow illustrating the various functions of the methods and systems of this disclosure according to one non-limiting embodiment. With reference to FIG. 5, "host system/environment" identifies functions typically performed by components that are not part of software set 100. With continued reference to FIG. 5, the "host system" performs the CTPA imaging study on the subject patient, checks that certain scan conditions are met, and generates the CTPA images (slices). These images, which can form the initial image set 10 described above, are then passed into software set 100 where there are received by the pre-processor 110. The quality of the CTPA images is checked to ensure, e.g., that sufficient contrast enhancement is met. If the quality criteria are met, the external interface can modify the images through segmentation (e.g., to generate modified image set 30), which is then passed to each of the CMA module 200, LPA module 300, and CPAA module 400. The results of each of these modules are then passed classifier module 500. At various points, the software checks for patient history, including history of pulmonary embolism (PE) and deep vein thrombosis (DVT). In this embodiment, Classifier module 500 is configured to require patient history in order to enter the CTEPH decision tree and CPAA 400 module is configured to require patient history before an output is generated from that module. Once classifier module 500 issues an output from the CTEPH decision tree, the output can be combined with other information to generate a report by post-processing module 600. The report (e.g., a report of the format of FIGS. 3A-3D) can be displayed to a radiologist on a workstation and, if approved, sent to PACS 8.

Figure 6:
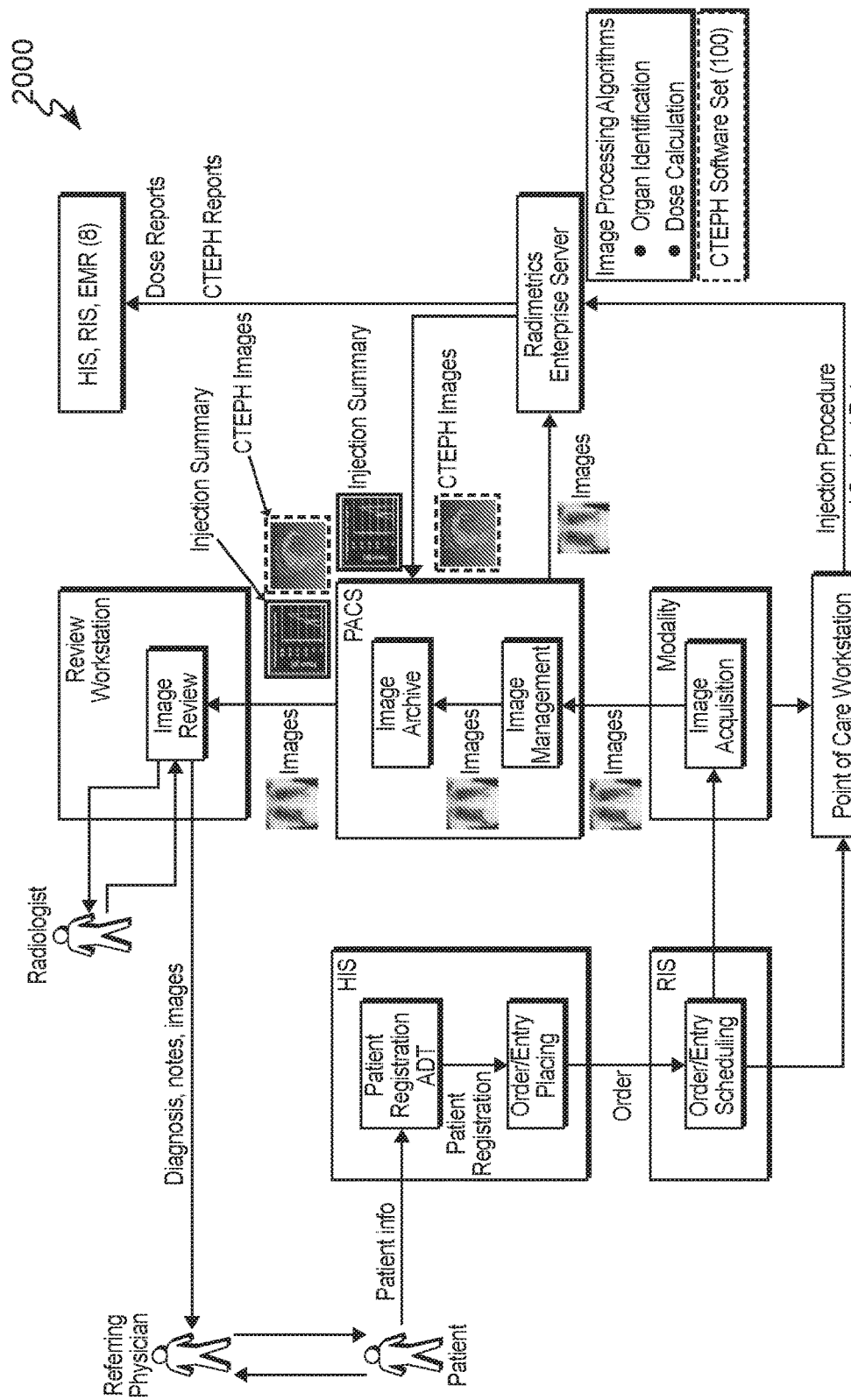
FIG. 6 illustrates a workflow diagram of a clinical setting incorporating the system of the present disclosure according to one non-limiting embodiment of the present disclosure.

The system 1 and software set 100, as well as the method 1000 performed by these components, may be implemented with computed tomography (CT) scanning systems in a variety of ways in various clinical settings. For example, with reference to FIG. 6, software set 100 can be implemented in a clinical setting 2000 via an enterprise server, such as a Radimetrics™ workstation, which is available from Bayer HealthCare LLC, in an imaging suite equipped with an injector, such as the MEDRAD® Stellant CT Injection System and the Certegra® Workstation, both also available from Bayer. As shown in FIG. 6, the referring physician communicates with the patient to develop an imaging plan to perform a medical imaging procedure. The imaging plan can include the type of procedure that will be conducted, as well as details related thereto, such as the type of contrast and the protocols to be implemented by the medical injector and/or imaging modality (e.g., CT scanner). The patient, upon arrival at the imaging clinic (e.g., hospital), can register and patient information can be entered into the hospital information system (HIS). Upon patient registration, the imaging procedure can be placed and scheduled. The details of the imaging procedure (e.g., the injection and imaging protocols) can then be sent to an imaging suite which can comprise a point of care workstation, injector, and/or imaging modality. A technician can then perform the imaging procedure on the subject patient, and the results of that procedure can be sent to other systems and subsystems within the clinical setting. In the example of FIG. 6, the images generated during the imaging procedure (which can be the initial image set 10 described above) can be sent to the picture archiving and communication system (PACS), which can perform image archive and management functions consistent with its typical method of operation. The initial image set 10, as well as other details about the imaging procedure such as the injection protocol and/or contrast data, can also be sent to the enterprise server, depicted in FIG. 6 as a Radimetrics™ Enterprise Server. In the embodiment of FIG. 6, image processing software resides on the enterprise server, including software set 100 described above. Enterprise server performs image processing according to these algorithms and generates, for example, injection summary and CTEPH related data, including CTEPH reports. The CTEPH reports can be those reports described above in connection with the post-processing module 600. As depicted in FIG. 6, this information can be communicated to the PACS where it can be archived and stored. In addition, the information generated by the enterprise server can be provided to a review workstation that can include a display screen for presenting the information in a visually perceptible form for review by a radiologist and/or other medical professional. For example, the workstation can display CTEPH reports of the form shown in FIGS. 3A-3D, and these reports can be reviewed by a radiologist to assist with the diagnosis and/or treatment of the patient. The diagnosis, notes, and images reviewed and/or generated by the radiologist can then be communicated to the referring physician and shared with the patient, thereby completing the information loop and providing the patient with valuable medical information, including information about whether the patient may be affected by CTEPH.

Figure 7:
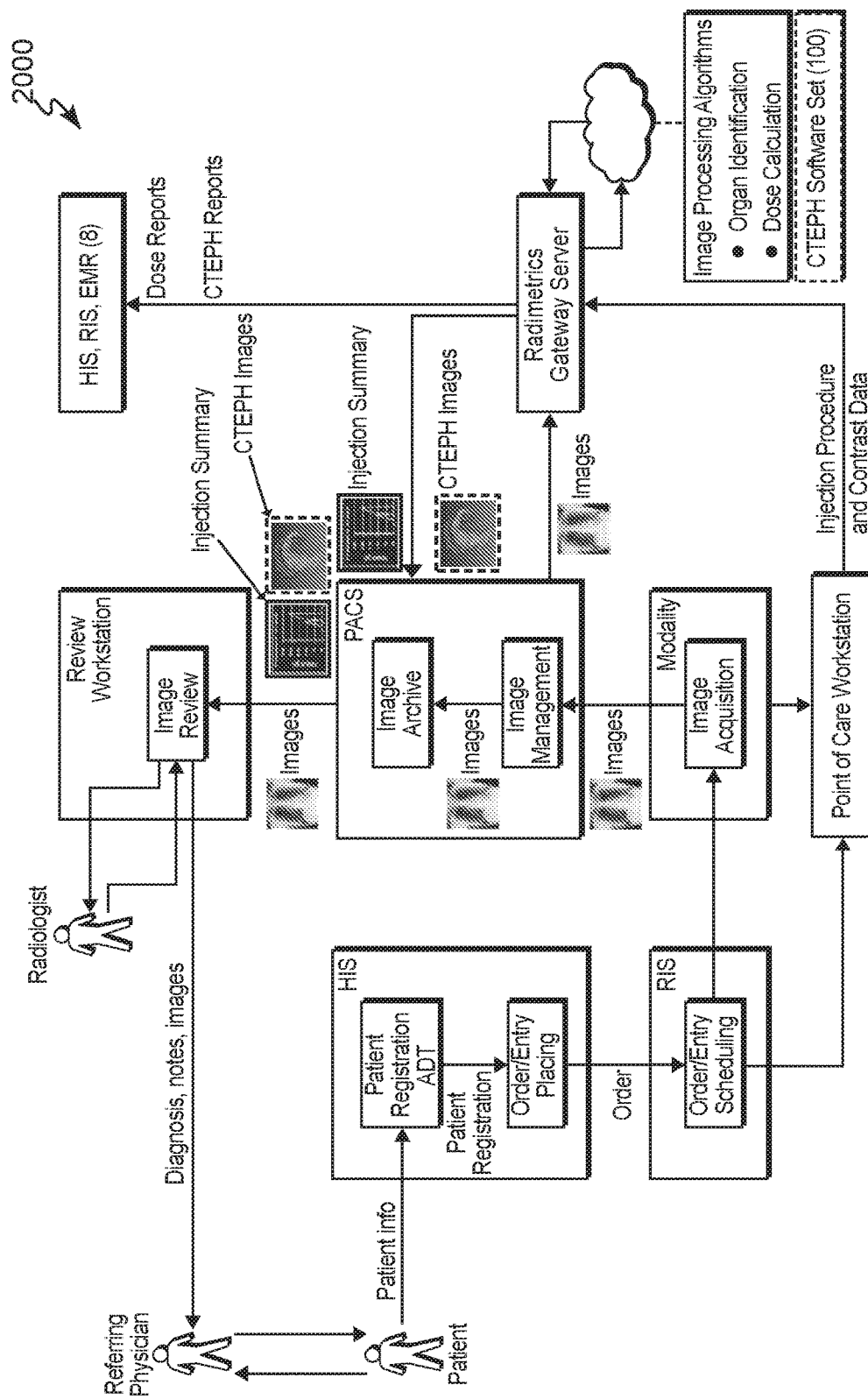
FIG. 7 illustrates a workflow diagram of a clinical setting incorporating the system of the present disclosure according to another non-limiting embodiment of the present disclosure.

In another example, FIG. 7 illustrates software set 100 implemented in a clinical setting 2000 having an imaging suite equipped with an injector, such as the MEDRAD® Stellant CT Injection System and the Certegra® Workstation via a server-client (i.e., cloud) implementation. The workflow of FIG. 7 generally follows the same process as described above for FIG. 6. However, in this embodiment, the enterprise server has been replaced by a gateway server (e.g., Radimetrics™ Gateway Server) which functions as a connection point between the clinic and cloud-based image processing software. In this particular embodiment, the cloud-based image processing software includes software set 100. The cloud-based implementation provides certain advantages over the enterprise (local) embodiment of FIG. 6, including allowing for better data sharing across different clinics and sharing of software resources, which can reduce the costs and maintenance requirements when compared with multiple local servers each running its own copy of the software. Reports and other information generated "in the cloud" can then be returned to the clinic and introduced back into the workflow, where it can be stored, reviewed, and used in the same manner as described above for FIG. 6.

Figure 8:
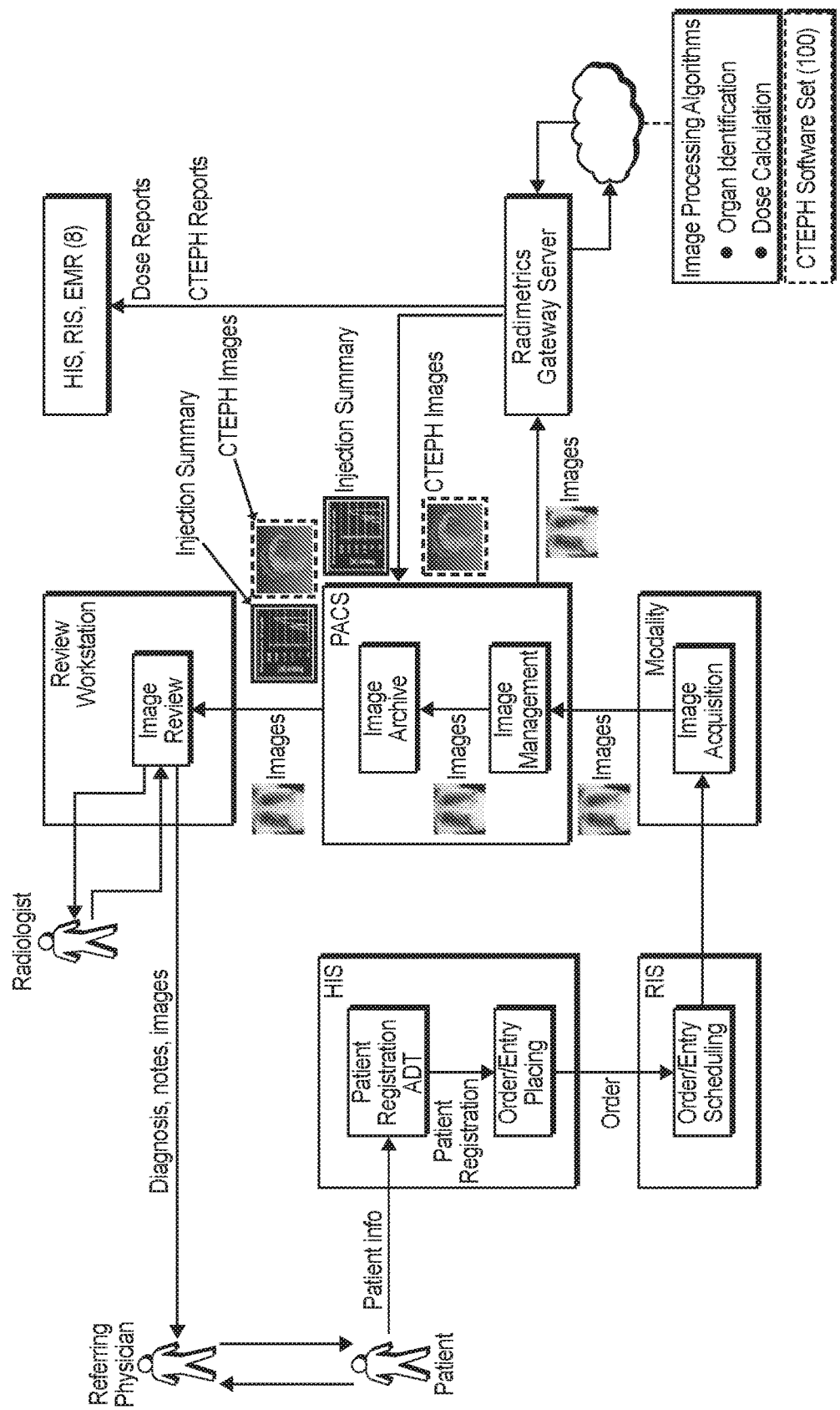
FIG. 8 illustrates a workflow diagram of a clinical setting incorporating the system of the present disclosure according to another non-limiting embodiment of the present disclosure.

In yet another example, FIG. 8 shows software set 100 implemented in clinical setting 2000 via a cloud implementation in an imaging suite not equipped with a contrast media injection system or any informatics workstation designed to operate therewith. The workflow of FIG. 8 generally follows that of FIG. 7, although this workflow may be more representative of an imaging procedure that does require a contrast injection.

The system 1 and software set 100 can thus be implemented in wide variety of CT imaging suites in which a variety of contrast media injection systems may be used. The system 1 and software set 100 can be applied to CT imaging studies whether or not contrast media is used to enhance the images thereof.

Software set 100 can be offered as a software package or product capable of being run on, and/or integrated with, any one or more of the systems typically found in a healthcare enterprise. Examples of such systems include the CT scanning systems offered by original equipment manufacturers (OEMs) such as GE, Siemens and Philips, the PACS systems offered by those vendors and so many others, and injector systems offered by Bayer HealthCare LLC (e.g., MEDRAD® Stellant CT Injection System, MEDRAD® Stellant FLEX CT Injection System and MEDRAD® Centargo CT Injection System) and others. As a software package, software set 100 can also be integrated with the IT systems typically operated by most healthcare enterprises.

The report discussed above in connection with the post-processing unit 600 can be displayed on a workstation of FIGS. 6-8 or other suitable display, and may be implemented in a variety of ways. For example, the report may be implemented as a multi-tab/page report having one or more sections as follows: (i) a "Report Summary" section; (ii) a "Patient History" section; (iii) a "3D View" section to show detailed views of the cardiac region, the pulmonary vasculature and/or the lungs; (iv) a "Pulmonary Vessels" section; (v) a "Heart Section" section; (vi) a "Lungs" section; and (vii) a "Scan Quality" section in which metrics and other information pertaining to the quality of the CT imaging scans may be presented.

In another non-limiting embodiment, system 1 and software set 100 can be implemented as part of a system comprising a processor and a memory. The processor including at least one of a central processing unit (CPU), a graphics processing unit (GPU) and a tensor processing unit (TPU). The memory is used for storing an application program that is configured to perform, when executed by the processor, an operation for identifying one or more pathologic signs of disease.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

The invention claimed is:

1. A system, comprising:
   a processor; and
   a memory storing an application program configured to perform, when executed by the processor, an operation for assessing a likelihood of chronic thromboembolic pulmonary hypertension within a subject patient based upon an analysis of characteristics indicative of chronic thromboembolic pulmonary hypertension within an imaging study of the subject patient, the operation comprising:
      receiving an initial image set comprising a plurality of images from the imaging study of the subject patient and modifying one or more of the plurality of images from the initial image set to generate a modified image set comprising one or more modified images;
      identifying in at least one of the modified images of the modified image set one or more characteristics of one or more anatomical structures within a cardiac region of the subject patient indicative of chronic thromboembolic pulmonary hypertension;

identifying in at least one of the modified images of the modified image set one or more characteristics of a pulmonary vasculature of the subject patient indicative of chronic thromboembolic pulmonary hypertension;

identifying in at least one of the modified images of the modified image set one or more characteristics of a chronic abnormality in a lung of the subject patient indicative of chronic thromboembolic pulmonary hypertension; and assessing the one or more characteristics identified in the modified image set of (i) the one or more anatomical structures within the cardiac region of the subject patient indicative of chronic thromboembolic pulmonary hypertension, (ii) the pulmonary vasculature of the subject patient indicative of chronic thromboembolic pulmonary hypertension, and (iii) the chronic abnormality in the lung of the subject patient indicative of chronic thromboembolic pulmonary hypertension and computing, from this assessment, the likelihood of chronic thromboembolic pulmonary hypertension within the subject patient.

2. The system of claim 1, wherein the modified image set is generated by an image processing algorithm trained via machine learning to identify, within the plurality of images of the initial image set, images that comprise one or more target organs.

3. The system of claim 2, wherein the image processing algorithm is further configured to generate one or more of the modified images by cropping one or more images from the initial image set that comprise the one or more target organs to reduce a size of the one or more images from the initial image set.

4. The system of claim 3, wherein the image processing algorithm is further configured to crop the one or more images from the initial image set by drawing a boundary box around the one or more target organs and removing areas of the image that are outside of the boundary box to reduce the size of the one or more images from the initial image set.

5. The system of claim 2, wherein the one or more target organs are the heart and/or lungs.

6. The system of claim 1, wherein identifying the one or more characteristics of the one or more anatomical structures within a cardiac region of the subject patient comprises performing, by a first analysis algorithm trained via machine learning, image segmentation on one or more of the modified images to locate the one or more anatomical structures within the one or more modified images.

7. The system of claim 6, wherein the one or more anatomical structures comprise at least one of a left ventricle, a right ventricle, a pulmonary aorta, and an ascending aorta.

8. The system of claim 6, wherein identifying the one or more characteristics of the one or more anatomical structures within a cardiac region of the subject patient further comprises measuring one or more dimensions of the one or more anatomical structures.

9. The system of claim 8, wherein the dimensions comprise one or more of a volume of a left ventricle, a radius of the left ventricle, a volume of the right ventricle, a radius of the right ventricle, a volume of the pulmonary aorta, a radius of the pulmonary aorta, a volume of the ascending aorta, and a radius of the ascending aorta.

10. The system of claim 1, wherein identifying the one or more characteristics of the pulmonary vasculature of the subject patient comprises identifying, by a second analysis algorithm trained via machine learning, a perfusion abnormality within the one or more modified images.

11. The system of claim 10, wherein identifying the perfusion abnormality within the one or more modified images comprises analyzing a measured contrast attenuation within a lung parenchyma of the subject patient.

12. The system of claim 11, wherein identifying the perfusion abnormality within the one or more modified images comprises: segmenting each of the one or more modified images into voxels; reviewing each voxel to predict whether the voxel is positive or negative for a likelihood of the perfusion abnormality; and aggregating the results of the reviewing step to determine the presence of the perfusion abnormality based at least on part on the proximity of voxels that are positive for the likelihood of the perfusion abnormality relative to one another.

13. The system of claim 1, wherein identifying the one or more characteristics of the chronic abnormality in the lung of the subject patient comprises identifying, by a third analysis algorithm trained via machine learning, a vascular abnormality within the one or more modified images.

14. The system of claim 13, wherein identifying the vascular abnormality within the one or more modified images comprises: segmenting each of the one or more modified images into voxels; reviewing each voxel to predict a risk of the vascular abnormality within the voxel; aggregating the results of the reviewing step to determine a location of voxels predicted to exceed a threshold risk factor; and assessing, based at least in part upon a proximity of voxels determined to exceed the threshold risk factor relative to one another, the presence of the vascular abnormality within the one or more modified images.

15. The system of claim 13, wherein identifying the one or more characteristics of the chronic abnormality in the lung of the subject patient further comprises receiving patient information indicative of whether the subject patient has a history of pulmonary embolisms.

16. The system of claim 13, wherein the operation further comprises identifying a location of the vascular abnormality and adding a visual indication on one or more of the modified images of the location of the vascular abnormality.

17. The system of claim 1, wherein computing the likelihood of chronic thromboembolic pulmonary hypertension within the subject patient comprises using a weighting and scoring algorithm trained via machine learning to generate a confidence weighting for each of the characteristics and computing, using the confidence weightings, an overall score representative of the likelihood of chronic thromboembolic pulmonary hypertension within the subject patient.

18. The system of claim 1, wherein the system further comprises a display screen, and wherein the operation further comprises generating a report comprising an indication of the likelihood of chronic thromboembolic pulmonary hypertension within the subject patient and displaying the report on the display screen.

19. A non-transitory computer-readable storage medium comprising processor-executable instructions with which to perform an operation for assessing a likelihood of chronic thromboembolic pulmonary hypertension within a subject patient based upon an analysis of characteristics indicative of chronic thromboembolic pulmonary hypertension within an imaging study of the subject patient, the operation comprising:

receiving an initial image set comprising a plurality of images from the imaging study of the subject patient and modifying one or more of the plurality of images from the initial image set to generate a modified image set comprising one or more modified images;

identifying in at least one of the modified images of the modified image set one or more characteristics of one or more anatomical structures within a cardiac region of the subject patient indicative of chronic thromboembolic pulmonary hypertension;

identifying in at least one of the modified images of the modified image set one or more characteristics of a pulmonary vasculature of the subject patient indicative of chronic thromboembolic pulmonary hypertension;

identifying in at least one of the modified images of the modified image set one or more characteristics of a chronic abnormality in a lung of the subject patient indicative of chronic thromboembolic pulmonary hypertension; and assessing the one or more characteristics identified in the modified image set of (i) the one or more anatomical structures within the cardiac region of the subject patient indicative of chronic thromboembolic pulmonary hypertension, (ii) the pulmonary vasculature of the subject patient indicative of chronic thromboembolic pulmonary hypertension, and (iii) the chronic abnormality in the lung of the subject patient indicative of chronic thromboembolic pulmonary hypertension and computing, from this assessment, the likelihood of chronic thromboembolic pulmonary hypertension within the subject patient.

20. The non-transitory computer-readable storage medium of claim 19, wherein the modified image set is generated by an image processing algorithm trained via machine learning to identify, within the plurality of images of the initial image set, images that comprise one or more target organs.

21. A system, comprising:
an imaging modality for performing an imaging study on a subject patient;
a hospital information system comprising a database storing information on a medical history of the subject patient;
a workstation comprising a display screen;
an image processing unit comprising a processor; and
a memory storing an application program configured to perform, when executed by the processor, an operation for assessing a likelihood of chronic thromboembolic pulmonary hypertension within the subject patient based upon an analysis of characteristics indicative of chronic thromboembolic pulmonary hypertension within the imaging study of the subject patient, the operation comprising:

receiving the initial image set comprising a plurality of images from the imaging study of the subject patient and modifying one or more of the plurality of images from the initial image set to generate a modified image set comprising one or more modified images;

identifying in at least one of the modified images of the modified image set one or more characteristics of one or more anatomical structures within a cardiac region of the subject patient indicative of chronic thromboembolic pulmonary hypertension;

identifying in at least one of the modified images of the modified image set one or more characteristics of a pulmonary vasculature of the subject patient indicative of chronic thromboembolic pulmonary hypertension;

identifying in at least one of the modified images of the modified image set one or more characteristics of a chronic abnormality in a lung of the subject patient indicative of chronic thromboembolic pulmonary hypertension; and assessing the one or more characteristics identified in the modified image set of (i) the one or more anatomical structures within the cardiac region of the subject patient indicative of chronic thromboembolic pulmonary hypertension, (ii) the pulmonary vasculature of the subject patient indicative of chronic thromboembolic pulmonary hypertension, and (iii) the chronic abnormality in the lung of the subject patient indicative of chronic thromboembolic pulmonary hypertension and computing, from this assessment, the likelihood of chronic thromboembolic pulmonary hypertension within the subject patient.

* * * * *

UNITED STATES PATENT AND TRADEMARK OFFICE
CERTIFICATE OF CORRECTION

| | | |
|---|---|---|
| PATENT NO. | : 12,002,203 B2 | Page 1 of 1 |
| APPLICATION NO. | : 17/434839 | |
| DATED | : June 4, 2024 | |
| INVENTOR(S) | : El Sayed et al. | |

It is certified that error appears in the above-identified patent and that said Letters Patent is hereby corrected as shown below:

On the Title Page

On Page 3, in Item (56), under "OTHER PUBLICATIONS", in Column 1, Line 20, delete "Unites" and insert -- Units --, therefor.

On Page 3, in Item (56), under "OTHER PUBLICATIONS", in Column 2, Line 20, delete "ISMRM,," and insert -- ISMRM, --, therefor.

On Page 3, in Item (56), under "OTHER PUBLICATIONS", in Column 2, Line 34, delete "Basics""," and insert -- Basics", --, therefor.

In the Specification

In Column 11, Line 50, delete "for in" and insert -- in --, therefor.

In Column 16, Line 27, delete "quantitative flow reserve (QFR)" and insert -- quantitative flow ratio (QFR) --, therefor.

In Column 22, Line 20, delete "there" and insert -- they --, therefor.

Signed and Sealed this
Twentieth Day of August, 2024

Katherine Kelly Vidal
*Director of the United States Patent and Trademark Office*